United States Patent [19]
Berger et al.

[11] Patent Number: 6,111,055
[45] Date of Patent: Aug. 29, 2000

[54] ESTER-TERMINATED POLYAMIDE GELS

[75] Inventors: Vivian Berger, Dumont; Charles R. Frihart, Lawrenceville, both of N.J.; Ronald L. Gordon, Springfield, Ga.; Jochen Heydel, Mahwah, N.J.; Richard C. MacQueen, Phillipsburg, N.J.; Mark S. Pavlin, Lawrenceville, N.J.; Virgil Williams, Brooklyn, N.Y.

[73] Assignees: Union Camp Corporation, Wayne; Bush Boake Allen, Montvale, both of N.J.

[21] Appl. No.: 08/939,034

[22] Filed: Sep. 26, 1997

Related U.S. Application Data

[63] Continuation-in-part of application No. 08/734,523, Oct. 18, 1996, Pat. No. 5,783,657.

[51] Int. Cl.[7] .......................... C08G 69/08; C08G 73/10; C08L 77/00
[52] U.S. Cl. .......................... 528/310; 528/272; 528/288; 528/292; 528/302; 528/324; 528/326; 528/339; 528/339.3; 528/344; 524/219; 524/606; 424/64; 424/66; 431/288; 431/289; 431/291; 44/265; 44/272; 44/275; 44/459
[58] Field of Search .......................... 528/272, 288, 528/292, 302, 310, 324, 326, 339, 339.3, 344; 44/265, 272, 275, 459; 524/219, 606; 431/288, 289, 291; 424/64, 66

[56] References Cited

U.S. PATENT DOCUMENTS

| | | | |
|---|---|---|---|
| 3,615,289 | 10/1991 | Felton | 44/7.5 |
| 3,645,705 | 2/1972 | Miller et al. | 44/7.5 |
| 3,741,711 | 6/1973 | Bryant | 431/125 |
| 3,819,342 | 6/1974 | Gunderman et al. | 44/7.5 |
| 4,051,159 | 9/1977 | Tsoucalas et al. | 260/404.5 |
| 4,115,370 | 9/1978 | Corrado | 260/22 CQ |
| 4,150,002 | 4/1979 | Drawert et al. | 260/18 |
| 4,341,671 | 7/1982 | Bolze et al. | 528/324 |
| 4,346,024 | 8/1982 | Coquard et al. | 524/219 |
| 4,369,284 | 1/1983 | Chen | 524/476 |
| 4,449,987 | 5/1984 | Lindauer | 44/7.5 |
| 4,552,693 | 11/1985 | Hussain et al. | 252/522 |
| 4,663,428 | 5/1987 | Okitu et al. | 528/324 |
| 5,132,355 | 7/1992 | Nahlovsky | 524/474 |
| 5,221,534 | 6/1993 | DesLauriers et al. | 424/78.03 |
| 5,578,089 | 11/1996 | Elsamaloty | 44/275 |
| 5,783,657 | 7/1998 | Pavlin et al. | 528/310 |

FOREIGN PATENT DOCUMENTS

| | | |
|---|---|---|
| WO 88/00603 | 1/1988 | WIPO . |
| WO 97/08282 | 3/1997 | WIPO . |

*Primary Examiner*—P. Hampton-Hightower
*Attorney, Agent, or Firm*—Seed and Berry LLP

[57] ABSTRACT

An ester-terminated dimer acid-based polyamide may be blended with a solvent to form a gel. The solvent may be flammable, and a wick may be added to the resulting gel so as to form a candle. Depending on the composition, the candle may be formed into a free standing pillar, or may be better suited to being placed in a container. The solvent may be mineral oil. A solid coating may be placed around the candle, for advantages including to enhance the mechanical stability of the gelled body, and to eliminate the tendency of a gel to have an oily feel and to accept noticeable fingerprints. The solvent which, in combination with the ester-terminated dimer acid-based polymer forms a gel, may be or include a fragrance material, an insecticide or an insect repellent. A wick may or may not be present in this gel, but in any event, the composition provides for the release of the fragrance, insecticide or insect-repellent.

69 Claims, 5 Drawing Sheets

ESTER-TERMINATED POLYAMIDE GELS

CROSS-REFERENCE TO RELATED APPLICATION

The present application is a continuation-in-part of U.S. application Ser. No. 08/734,523 filed Oct. 18, 1996, now U.S. Pat. No. 5,783,657, which is incorporated herein by reference in its entirety.

TECHNICAL FIELD OF THE INVENTION

The invention relates to gelled articles, and in particular to articles that are flammable, such as a candle, and/or contain and emit an active ingredient, such as fragrance, where the article may include an exterior coating.

BACKGROUND OF THE INVENTION

A common type of candle that sees widespread use consists of a wick embedded in a block of paraffin wax, where the wax provides the fuel for the burning candle. Paraffin has many properties that make it suitable for use in a candle. Paraffin as used in candles is typically highly refined and, at room temperature, is in a crystalline state. Crystalline paraffin is naturally white, and white paraffin candles are commonplace. Colorants may be added to these paraffin-based candles, to thereby achieve essentially any desired coloration. Paraffin-based candles are also rigid, and can be formed into a free-standing pillar structure. Such pillar candles, whether white or colored, can be placed atop candlesticks and the like, and are a popular consumer item. Paraffin is an inexpensive raw material, which makes it an economically-attractive ingredient for a candle. Perhaps unappreciated by consumers is that paraffin is also a good material from which to prepare a candle because it meets the rather stringent burning requirements for a candle, as discussed in more detail herein.

Paraffin-based candles have a significant drawback, however. Paraffin-based candles are neither transparent nor translucent, and in fact are opaque. Candle manufacturers have recognized an unmet need for transparent candles, and particularly transparent candles which can adopt the pillar form, ie., are rigid and self-supporting. Thus, the literature describes numerous attempts to prepare a satisfactory transparent pillar candle.

One approach has been to combine a thermoplastic polyamide resin with a solvent, where the polyamide resin is formed from dimer acid and acts as a gellant. Examples of this approach are found in, for example, U.S. Pat. Nos. 3,615,289; 3,645,705; 3,819,342 and 4,449,987. Candles made by this approach, which may be referred to as polyamide gel candles, have significant shortcomings which have limited their commercial acceptance. For example, such compositions are often not very transparent or even translucent, and may require the addition of a "clarifying agent" to achieve even a semi-transparent state (see, e.g., U.S. Pat. No. 3,819,342). In addition, such compositions are often not as hard as desired, and may require additives that increase stiffness and hardness in order to achieve even a short pillar form (see, e.g., U.S. Pat. No. 3,645,705), or are simply recommended for use in containers (see, e.g., U.S. Pat. No. 3,819,342).

Another significant problem with candles prepared with polyamide gellants is that they typically exhibit syneresis, where this term refers to the formation of liquid on the surface of a gel or colloidal suspension. In other words, droplets of solvent or other candle additive often form on the surfaces of a polyamide gel candle. Syneresis is a highly undesirable property in a candle because, among other reasons, 1) consumers don't want to touch a wet, oily candle; 2) the candle becomes more brittle as oil escapes; and 3) the droplets of liquid solvent/additives tend to burn quite quickly once the candle is lit, giving the candle a torch-like quality.

Syneresis is particularly pronounced when the candle incorporates fragrance: the fragrance is frequently observed to exude from the candle and exacerbate the flaring problem (as discussed in, e.g., U.S. Pat. No. 3,615,289). Thus, for example, U.S. Pat. No. 3,645,805 suggests using only a small amount of fragrance in a polyamide gel candle, while U.S. Pat. No. 3,615,289 recommends up to about 2 percent fragrance. When relatively high amounts of fragrance are incorporated into either a polyamide gel candle or the block copolymer gel candles discussed below, the fragrance is typically observed to separate from the candle matrix and pool on the top of the candle. This segregation of the fragrance leads to a flaring or flashing problem with gelled fragranced candles, so that these candles tend to bum in an "out of control" manner, which the prior art has yet to solve. Polyamide gel candles also tend to exhibit blooming, where this term identifies the formation of opaque regions on the candle's surface. Blooming causes a significant aesthetic defect (opaque regions) in a candle that is supposed to be transparent.

Basically, the phenomena of syneresis and blooming reflect the fact that the components of a polyamide gel candle are not sufficiently compatible with one another to maintain a homogeneous state. The prior art has both recognized this problem and attempted to solve it by various means. Two such approaches are the judicious choice of solvent (see, e.g., U.S. Pat. No. 3,819,342), and/or including additives in the candle composition, such as "anti-flaring" compounds (see, e.g., U.S. Pat. No. 3,615,289). These approaches have not been very successful in providing a candle which is desired by the public.

There are several other problems associated with the gel candles prepared with polyamide gellants. One such problem is the failure of the candle to have and/or retain a completely colorless clear appearance. More specifically, it is observed that these gel candles will typically develop an undesirable yellow hue over time and/or with burning. Another problem is that when a colorant has been added to a polyamide gel candle, the initial color of the candle can fade, possibly due to a reaction between the organic components of the candle and the colorant. Also, polyamide gel candles are often observed to form an irreversibly crosslinked structure, which is undesirable because once the molten composition is poured into the form of a candle, it cannot be remelted and repoured in instances where the original candle contained a structural defect.

In general, polyamide gel candles have serious shortcomings, and have not received wide commercial acceptance. An alternative approach to preparing a clear gel candle is to disperse block copolymers in a clear oil, where a preferred block copolymer is a rubber. Disclosures of this approach are found in, for example, U.S. Pat. No. 5,578,089 and PCT International Application No. PCT/US96/13993. According to the '089 patent, at least two components selected from the group consisting of diblock copolymers, triblock copolymers, radial copolymers, multiblock polymers and mixtures thereof may be used in combination with hydrocarbon oil to form a gel candle. PCT/US96/13993 is also directed to the use of various block copolymers, preferably thermoplastic rubbers, in combination with mineral oil to form a gel suitable for molding into a candle. Candles prepared by these technologies purportedly overcome many of the problems observed with polyamide gel candles.

However, the '089 patent mentions that while the candle may be free standing at room temperature, this patent also recommends that the candle is preferably supplied in a container. The '089 patent comments that a container is desirable because of the gel-like nature of the candle itself and its potential flowability when heated. The gel-like nature of the block copolymer candles is similar to the gel-like nature of the polyamide candles discussed above in that while a "free-standing" structure may be formed from each of these gels, such structures are "free-standing" only in the sense that Jell-O™, a well-known gelled food product, is free-standing. Thus, a portion of Jell-O™ may be placed on a plate and will maintain itself at some height above the plate, without being contained. In this sense, Jell-O™ and prior art gels are indeed free-standing. However, consumers desire candles with a free-standing pillar structure, and while such a structure might be made from a material with the consistency of Jell-O™, it would only precariously hold the pillar structure—one little tap and the pillar would flop over.

While the prior art has attempted to increase the rigidity of a gel candle (see, e.g., methyl esters as a stiffness additive as disclosed in U.S. Pat. No. 3,645,705), these attempts have either failed to provide the desired rigidity or have hurt other properties such as clarity, freedom from syneresis, and a self-perpetuating flame. For example, attempts to increase the rigidity of a gel candle may take an approach that causes a concomitant increase in the viscosity of the molten gel. A more viscous molten gel will tend to incorporate and retain more air bubbles. The presence of air bubbles in a cooled candle will cause the candle to have a translucent, rather than the desired transparent appearance.

Another reason why gel candles are often recommended for use in containers as opposed to being free-standing is due to the potential flowability of a gel candle when it is heated. Thus, when a prior art gel candle prepared from block copolymers is lit, the present inventors have observed that the melted gel runs over the sides of the candle and onto the supporting table, which is commercially undesirable. The present inventors speculate that this may be due to the thermal transfer within the candle material. Thus, the high temperature near the flame and wick of a gel candle is rapidly and efficiently transferred throughout the candle, so that the entire surface becomes heated above its melting point, producing too much melted candle. In any event, potential flowability issues associated with a gel candle can be avoided by placing the candle in a container, which is the approach often recommended in the prior art.

The use of a container is also desirable because of the problem of separating a gel candle from a mold. The thermoplastic polyamides that have been used in the prior art to form gel candles are often also useful as adhesives. And the block copolymers that have been used to form gel candles are rubbers which are very sticky when molten and/or when mixed with oils. Thus, the gel candles of the prior art are not easily removed from a mold (demolded), but instead may hold on tenaciously to the mold and be freed only with concomitant disfiguration of the surface of the candle. This disfiguration greatly reduces the candle's clarity which is a primary object of the use of a gel candle.

Therefore, and despite significant attention, there remains an unmet need in the art for a clear, free-standing, rigid and fragranced candle. The present invention provides a gel structure which is well suited for the preparation of a clear candle. In addition, the gel structure of the present invention may incorporate various active ingredients, such as fragrance, which can be emitted from the gel over a sustained period of time, thus providing a fragrant article such as a candle or air freshener. These and other related advantages of the present invention are disclosed below.

SUMMARY OF THE INVENTION

Briefly stated, the present invention provides a flammable article which includes a fuel and a solid coating, where the coating encases at least a portion of the fuel. The article may further contain a wick, where the wick is at least partially encased within the fuel. The fuel may be a wax or a gel. One fuel which may be used in the flammable article includes about 80 to 99 wt. % of a hydrocarbon oil, and about 1 to 20 wt. % of a blend of at least two different polymer members selected from the group consisting of diblock copolymers, triblock copolymers, radial block copolymers and multiblock copolymers, said composition including at least one diblock copolymer and at least one triblock copolymer, with said diblock and triblock polymers comprising segments of styrene monomer units and rubber monomer units. In another embodiment, the fuel includes from about 70% to about 98% by weight of a hydrocarbon oil, from about 2% to about 30% by weight a copolymer selected from the group consisting of a triblock, radial block and multiblock copolymer, and from 0 to about 10% by weight of a diblock copolymer.

Preferably, the fuel is entirely a gel, where the gel is formed from a gellant and a flammable solvent. The solvent preferably has a flash point ranging from about −15° C. to about 300° C. A preferred solvent is hydrocarbon oil, and a preferred article is a candle. Suitable gellants are one or more of a polyamide resin, an ester-terminated dimer acid-based polyamide (ETDABP) resin and a block copolymer. The polyamide resin is preferably the reaction product of reactants including dimer acid and diamine. The ester-terminated dimer acid-based polyamide resin is preferably the reaction product of reactants including dimer acid, diamine and monoalcohol. The block copolymer is preferably a styrene-butadiene-styrene or styrene-isoprene-styrene block copolymer.

The coating on the article is preferably a polymer selected from thermoplastic polymer and thermoset polymer. A suitable thermoplastic polymer is selected from polyamide resin, ester-terminated dimer acid-based polyamide resin and styrene-acrylic resin. The coating is preferably transparent, and in fact the fuel is also preferably transparent. The article may further contain an optional component selected from colorant, fragrance, insect repellent, insecticide, UV-inhibitor and antioxidant, where any of these optional components may be present in the fuel and/or coating.

The invention also provides a flammable article formed from components that include a gel, where the gel is formed from components including a gellant and a flammable solvent, where the gellant includes ester-terminated dimer acid-based polyamide (ETDABP). This gel in this article is preferably one or more of transparent, rigid, free from syneresis, and free-standing or positioned within a container. Preferably, the article also includes a wick, the wick at least partially encased by the gel, where such an article is a candle. The solvent for the candle preferably includes mineral oil. The ETDABP contributes 10–95%, and the solvent contributes 5–90% of the combined weight of the ETDABP and the solvent in a preferred article.

Optional components selected from fragrance, colorant, insect repellent, insecticide, antioxidant and/or UV-inhibitor may be present. In a preferred article, the ETDABP contributes 30–60%, the solvent contributes 40–70%, the fragrance contributes less than 50% and the colorant contributes less than 5% of the combined weight of the ETDABP, solvent, fragrance and colorant. In another preferred article, the ETDABP contributes 10–30%, the solvent contributes 65–80%, the fragrance contributes less than 50% and the colorant contributes less than 1% of the combined weight of the ETDABP, solvent, fragrance and colorant. In preferred ETDABPs, there is an amide:ester ratio of from 9:1 to 1:1.

The ETDABP in the above-described articles preferably has the formula

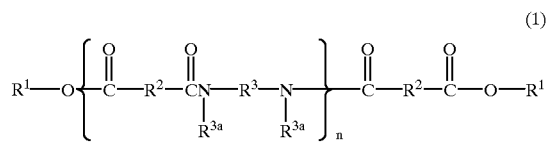

wherein, n designates a number of repeating units such that ester groups constitute from 10% to 50% of the total of the ester and amide groups;

$R^1$ at each occurrence is independently selected from hydrocarbyl groups;

$R^2$ at each occurrence is independently selected from a $C_{2-42}$ hydrocarbon group with the proviso that at least 10% of the $R^2$ groups have 30–42 carbon atoms;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^{3a}$ or $R^3$—N—$R^{3a}$.

In preferred embodiments, the ETDABP of formula (a) has $R^1$ at each occurrence being independently selected from an alkyl or alkenyl group containing at least 4 carbon atoms; $R^2$ at each occurrence being independently selected from a $C_{4-42}$ hydrocarbon group with the proviso that at least 50% of the $R^2$ groups have 30–42 carbon atoms; and $R^{3a}$ at each occurrence being independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen. Preferably, ester groups constitute from 20% to 35% of the total of the ester and amide groups.

In another preferred embodiment, $R^1$ in formula (1) is a $C_{12-22}$ alkyl group and $R^2$ is a $C_{30-42}$ hydrocarbon group having the structure of polymerized fatty acid with the carboxylic acid groups removed. In still another preferred embodiment, between 1% and 50% of the $R^2$ groups are a $C_{4-19}$ hydrocarbon group, $R^3$ is a $C_{2-36}$ hydrocarbon group and $R^{3a}$ is hydrogen. In still another preferred embodiment, $R^{3a}$ is hydrogen and at least 1% of the $R^3$ groups are polyalkylene oxide. In another preferred embodiment, at least 1% of the —N($R^{3a}$)—$R^3$—N($R^{3a}$)— groups are independently selected from

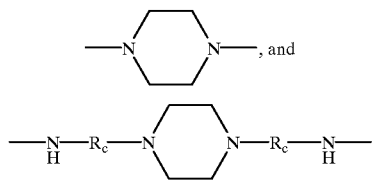

polyalkylene amine, wherein $R_c$ is a $C_{1-3}$ alkyl group.

In another aspect, the invention provides an article that includes a flammable solvent with a flash point ranging from about −15° C. to about 300° C. and an ester-terminated polyamide of formula (1) as defined above. This article may further contain a wick. The flash point of the solvent may range from about 40° C. to about 90° C. There is preferably a coating on at least a portion of the article's surface, where a preferred coating material is a dimer acid-based polyamide.

The invention also provides a flammable article which includes ester-terminated dimer acid-based polyamide (ETDABP) and solvent, the solvent having a flash point ranging from about −15° C. to about 300° C. and the ester-terminated dimer acid-derived polyamide being prepared by a method comprising reacting x equivalents of carboxylic acid from diacid or a reactive equivalent thereof, y equivalents of amine from diamine and z equivalents of hydroxyl from monoalcohol or a reactive equivalent thereof, wherein at least about 10% of the carboxylic acid equivalents are from polymerized fatty acid, and monoalcohol is substantially the only monofunctional reactant used to form the gellant, wherein each of x, y and z is greater than 0. This article may further contain a wick. In a preferred embodiment, $0.9 \leq \{x/(y+z)\} \leq 1.1$, and $0.1 \leq \{z/(y+z)\} \leq 0.7$. As in the articles described previously, this article may further contain a solid coating on at least a portion of the surface thereof, and/or may contain an optional component selected from colorant, fragrance, insect repellent, insecticide, or preservative such as antioxidant and UV-inhibitor.

The invention also provides a composition that emits an active substance over an extended period, where the composition includes ester-terminated dimer acid-based polyamide (ETDABP) and an active substance, and the composition has the consistency of a gel. A preferred ETDABP has the formula (1) above. The composition may be present within a container, or it may be free-standing as, for example, a stick. A preferred composition includes fragrance as the active substance, where suitable fragrances are any of menthol, methyl salicylate and eucalyptus. Another preferred active substance is selected from an insecticide and an insect-repellent. The composition may have a solid polymer coating present on at least a portion of the gel's surface. A preferred composition is transparent. The composition may further contain a colorant.

The invention also provides a method of forming a coated article. The method includes the steps of providing a gel structure having an exterior surface, and then applying a coating to the exterior surface. The coating may be applied by any of (a) spraying the coating onto the exterior surface; (b) dipping the gel structure into a solvent-containing coating composition; or (c) dipping the gel structure into a solvent-free molten coating composition.

These and related aspects of the invention are described further below.

DETAILED DESCRIPTION OF THE INVENTION

Figure 1:
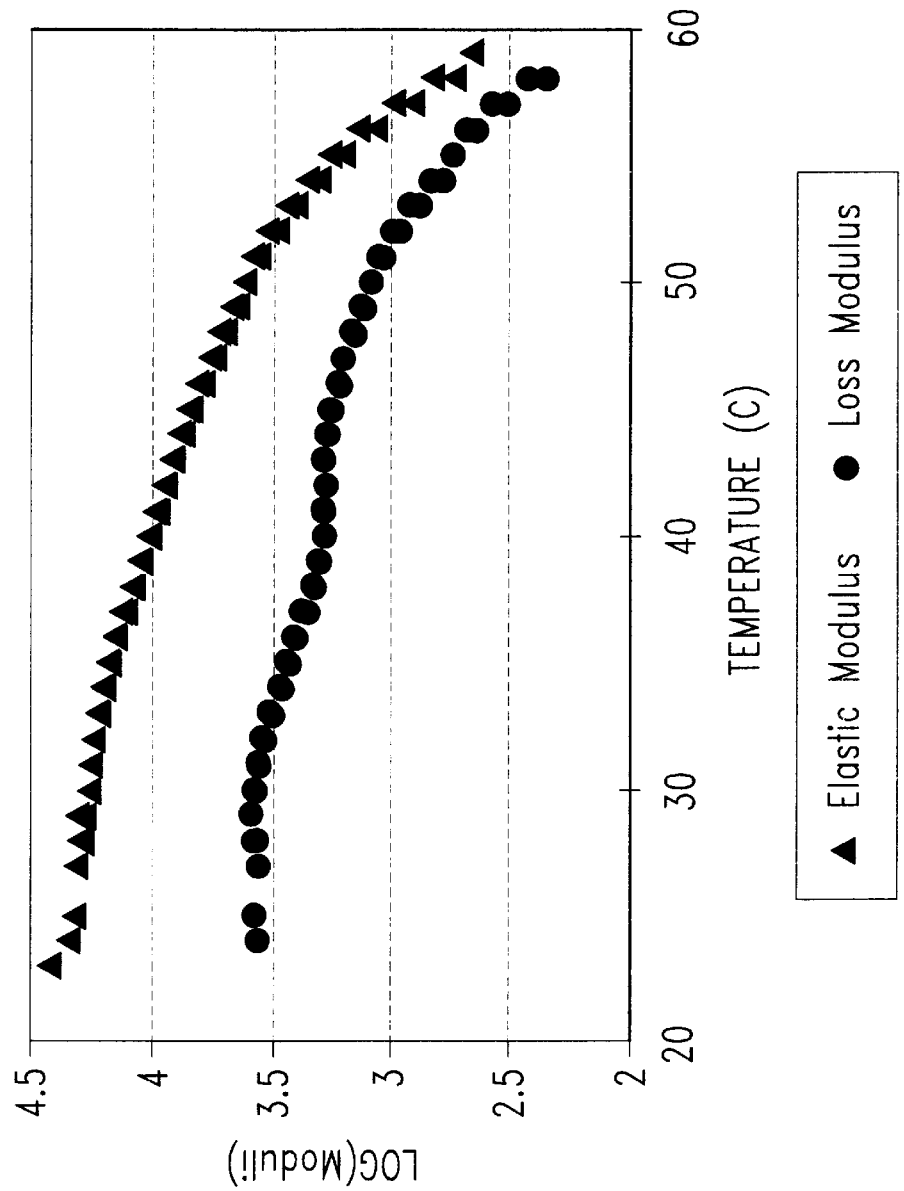
FIG. 1 is graphical representation of the effect of temperature on rheology for a gelled hydrocarbon of the invention.

The present invention provides a gelled composition that is stable, transparent and rigid. The composition is formed, at least in part, of a gellant in combination with a solvent, where this combination forms the gel. The gellant is preferably ester-terminated dimer acid-based polyamide (ETDABP) and is more preferably ester-terminated polyamide (ETPA), where ETPA is a preferred ETDABP.

As used herein, ETDABP refers to those compositions which are formed upon reaction of dimer acid, diamine and monoalcohol. Before describing the structure in detail, it is important to note that ETDABP may be formed from reactants other than dimer acid, diamine and monoalcohol, however, an ETDABP of the present invention will have the same, or essentially the same structural composition as is achieved by the reaction between dimer acid, diamine and monoalcohol. In other words, it is not necessary to use dimer acid, diamine and monoalcohol in forming an ETDABP of the present invention, however, ETDABP has the structure which would result upon reacting dimer acid, diamine and monoalcohol. For example, reactive equivalents of dimer acid, diamine and/or monoalcohol could be reacted together to provide an ETDABP of the invention.

Thus, reactive equivalents of diacids and/or diamines may be used in the invention to form ETDABP. For example, diesters may be substituted for some or all of the diacid, where "diesters" refers to the esterification product of diacid with hydroxyl-containing molecules. However, such diesters are preferably prepared from relatively volatile hydroxyl-containing molecules, in order that the hydroxyl-containing molecule may be easily removed from the reaction vessel subsequent to monoalcohol and/or diamine (both as defined herein) reacting with the diester. A lower alkyl diester, e.g., the esterification or diesterification product of diacid as defined herein and a $C_{1-4}$ monohydric alcohol (e.g., methanol, ethanol, propanol and butanol), may be used in place of some or all of the diacid in the ETDABP gellant-forming reaction of the invention. The acid halide of the diacid may likewise be employed in place of some or all of the diacid, however such a material is typically much more expensive and difficult to handle compared to the diacid, and thus the diacid is preferred. Likewise, the monoalcohol may be esterified with a volatile acid, e.g., acetic acid, prior to being employed in the ETDABP gellant-forming reaction of the invention. While such reactive equivalents may be employed in the reaction, their presence is not preferred because such equivalents introduce undesired reactive groups into the reaction vessel.

The preferred reactants used to form ETDABP will now be described.

Dimer acid (also known as polymerized fatty acid) is a well known material of commerce, and thus need not be described in great detail. Polymerized fatty acid is typically formed by heating long-chain unsaturated fatty acids, e.g., $C_{18}$ monocarboxylic acids, to about 200–250° C. in the presence of a clay catalyst in order that the fatty acids polymerize. The polymerization product typically comprises dimer acid, i.e., $C_{36}$ dicarboxylic acid formed by dimerization of the fatty acid, and trimer acid, i.e., $C_{54}$ tricarboxylic acid formed by trimerization of the fatty acid. Polymerized fatty acid is typically a mixture of structures, where individual dimer acids may be saturated, unsaturated, cyclic, acyclic, etc. A more detailed discussion of fatty acid polymerization may be found in, e.g., U.S. Pat. No. 3,157,681 and *Naval Stores—Production, Chemistry and Utilization*, D. F. Zinkel and J. Russell (eds.), Pulp. Chem. Assoc. Inc., 1989, Chapter 23.

Because fatty acid polymerization typically forms much more dimer acid than trimer acid, those skilled in the art sometimes refer to polymerized fatty acid as dimer acid, even though some trimer acid, and even higher polymerization products, may be present in admixture with the dimer acid. For preparing an ETDABP, it is preferred that the polymerized fatty acid contain less than about 10 weight percent of trimer acid, based on the total weight of the polymerized fatty acid, and that dimer acid constitute at least about 90 weight percent of the polymerized fatty acid. More preferably, the dimer acid constitutes essentially all of the polymerized fatty acid.

Typical unsaturated fatty acids used to form polymerized fatty acid include oleic acid, linoleic acid, linolenic acid, etc. Tall oil fatty acid, which is a mixture containing long-chain unsaturated fatty acids obtained as a byproduct of the wood pulping process, is preferred for preparing polymerized fatty acid useful for preparing ETDABPs. While tall oil fatty acid is a preferred source of long-chain fatty acid, the polymerized fatty acid may alternatively be prepared by polymerization of unsaturated fatty acids from other sources, e.g., soybeans or canola. The polymerized fatty acid useful in forming ETDABP is a liquid, with an acid number on the order of about 180 to about 200.

The polymerized fatty acid may be hydrogenated prior to being used in the ETDABP-forming reaction. Hydrogenation tends to provide for a slightly higher melting point for the inventive gellant, as well as provide the gellant with greater oxidative and color stability. Hydrogenated polymerized fatty acid also tends to provide for a lighter colored ETDABP, and is a preferred polymerized fatty acid for use in the practice of the present invention. Polymerized fatty acid, dimer acid, and hydrogenated versions thereof may be obtained from a number of commercial suppliers. For example, Union Camp Corporation (Wayne, N.J.) sells polymerized fatty acid under their UNIDYME® trademark.

The diamine reactant has two amine groups, both of which are preferably primary amines, and may be represented by the formula $HN(R^{3a})$—$R^3$—$N(R^{3a})H$. $R^{3a}$ is preferably hydrogen, but may also be an alkyl group or may also join together with $R^3$ or another $R^{3a}$ to form a heterocyclic structure. Diamines wherein $R^{3a}$ is not hydrogen, and/or wherein $R^3$ is not a hydrocarbon, are referred to herein as co-diamines. When present, co-diamines are preferably used in a minor amount compared to the diamines. $R^3$ may be a hydrocarbon group having at least two carbon atoms, where the carbon atoms may be arranged in a linear, branched or cyclic fashion, and the group may be saturated or contain unsaturation. Thus, $R^3$ may be aliphatic or aromatic. Preferred $R^3$ hydrocarbon groups have 2 to 36 carbon atoms, more preferred $R^3$ hydrocarbon groups have 2 to 12 carbon atoms, and still more preferred $R^3$ hydrocarbon groups have 2 to 6 carbon atoms.

Exemplary diamines having hydrocarbon $R^3$ groups, which are commercially available and may be used in the present invention include, without limitation, ethylenediamine (EDA), 1,2-diaminopropane, 1,3-diaminopropane, 1,4-diaminobutane, 1,2-diamino-2-methylpropane, 1,3-diaminopentane, 1,5-diaminopentane, 2,2-dimethyl-1,3-propanediamine, 1,6-hexanediamine (also known as hexamethylenediamine, HMDA), 2-methyl-1,5-pentanediamine, 1,7-diaminoheptane, 1,8-diaminooctane, 2,5-dimethyl-2,5-hexanediamine, 1,9-diaminononane, 1,10-diaminodecane, 1,12-diaminododecane, diaminophenanthrene (all isomers, including 9,10), 4,4'-methylenebis(cyclohexylamine), 2,7-diaminofluorene, phenylene diamine (1,2; 1,3 and/or 1,4 isomers), adamantane diamine, 2,4,6-trimethyl-1,3-phenylenediamine, 1,3-cyclohexanebis(methylamine), 1,8-diamino-p-menthane, 2,3,5,6-tetramethyl-1,4-phenylenediamine, diaminonaphthalene (all isomers, including 1,5; 1,8; and 2,3) and 4-amino-2,2,6,6-tetramethylpiperidine.

Suitable aromatic diamines (by which is meant molecules having two reactive, preferably primary amine groups ($-NH_2$) and at least one aromatic ring ("Ar")) include xylene diamine and naphthalene diamine (all isomers).

The $R^3$ group of the diamine may contain oxygen atoms in the form of a polyalkylene oxide group, in which case the diamine may be referred to as a co-diamine. Exemplary polyalkylene oxide-based co-diamines include, without limitation, the JEFFAMINE™ diamines, i.e., poly(alkyleneoxy)diamines from Huntsman Chemical, Inc. (Houston, Tex.), also known as polyether diamines. Preferred polyalkylene oxide-containing co-diamines are the JEFFAMINE™ ED and D series diamines. Ether-containing $R^3$ groups are not preferred, as they tend to lower the melting point of the gellant to an undesirable extent. However, a mixture formed from small amounts of a polyalkylene oxide-based diamine with a major amount of a hydrocarbon-based diamine is well-suited for use in the invention. In general, the diamine reactant may be a pure diamine as described above, or a mixture of such diamines.

The $R^3$ group of the diamine may contain nitrogen atoms, where these nitrogen atoms are preferably secondary or tertiary nitrogen atoms. A typical nitrogen atom-containing $R^3$ group having secondary nitrogen atoms is a polyalkylene amine, i.e., a group containing alternating alkylene groups and amine groups (i.e., $-NH-$ groups). The alkylene group is preferably ethylene, ie., $-CH_2CH_2-$, and the polyalkylene amine may be represented by the formula $NH_2-(CH_2CH_2NH)_mCH_2CH_2-NH_2$ wherein m is an integer from 1 to about 5. Diethylenetriamine (DETA) and triethylenetetraamine (TETA) are representative examples. When the diamine contains two primary amines in addition to secondary amines, the ETDABP-forming reaction is preferably conducted at relatively low temperature, so that the primary amines (in preference to the secondary amines) react with the diacid component.

However, the nitrogen atoms in the nitrogen-containing $R^3$ group may also be present as tertiary nitrogen atoms, e.g., they may be present in a heterocycle of the formula:

wherein $R_c$ is a $C_{1-3}$ alkyl group. Bis(aminoethyl)-N,N'-piperazine and bis(aminopropyl)-N,N'-piperazine may be used to introduce these $R^3$ groups into an ETDABP, and these are exemplary co-diamines according to the invention. In addition, the co-diamine may have one primary amine group and one secondary amine group (e.g., N-ethylethylenediamine or 1-(2-aminoethyl)piperazine). Generally, it is preferred that amine compounds having secondary amines not be present in the reaction mixture to any great extent, because their incorporation into an ester-terminated dimer acid-based polyamide tends to provide for poorer gelling ability of the ETDABP.

In general, the diamine reactant may have the formula $HN(R^{3a})-R^3-N(R^{3a})H$ wherein $R^{3a}$ is preferably hydrogen, but may also be $C_{1-10}$alkyl, preferably $C_{1-5}$alkyl, and more preferably $C_{1-3}$alkyl. In addition, $R^{3a}$ may join together with $R^3$ or another $R^{3a}$ group to form a heterocyclic structure. For example, when piperazine is used as a co-diamine, the two $R^{3a}$ groups in the $HN(R^{3a})-R^3-NH(R^{3a})$ structure have joined together to form an ethylene bridge.

The monoalcohol may be represented by the formula $R^1-OH$, wherein $R^1$ is a hydrocarbon group, preferably but not necessarily having at least four carbon atoms. Thus, the monoalcohol can also be described as a monohydric alcohol. $R^1$ is preferably a $C_{1-36}$ hydrocarbon, more preferably a $C_{12-24}$ hydrocarbon, still more preferably is a $C_{16-22}$ hydrocarbon, and yet still more preferably is a $C_{18}$ hydrocarbon. As used herein, the term $C_{1-36}$ refers to a hydrocarbon group having at least 1, but not more than 36 carbon atoms, and similar terms have an analogous meaning. The carbon atoms of the hydrocarbon group may be arranged in a linear, branched or cyclic fashion, and the group may be saturated or unsaturated. However, $R^1$ is preferably linear, with the hydroxyl group located on a terminal carbon atom, i.e., the monoalcohol is a primary monoalcohol. Thus, 1-dodecanol, 1-tetradecanol, 1-hexadecanol (cetyl alcohol), 1-octadecanol (stearyl alcohol), 1-eicosanol (arachidyl alcohol) and 1-docosanol (behenyl alcohol) are preferred monoalcohols for preparing an ETDABP, where names in parentheses are common or trivial names by which these monoalcohols are known. While the monoalcohol has been exemplified with saturated alkyl groups, the monoalcohol may alternatively contain an alkenyl group, ie., an alkyl group having unsaturation between at least two adjacent carbon atoms. One or a mixture of these alcohols may be used to prepare an ETDABP gellant.

Another monoalcohol reactant suited for the invention is a so-called Guerbet alcohol. Guerbet alcohols have the general formula $H-C(Ra)(Rb)-CH_2-OH$ wherein Ra and Rb may be the same or different and preferably represent a $C_{6-12}$ hydrocarbon group. Further discussion of Guerbet alcohols may be found in, e.g., "Dictionary For Auxiliaries For Pharmacy, Cosmetics And Related Fields," H. P. Fiedler, $3^{rd}$ Ed., 1989, Editio Cantor Aulendorf. 2-Hexadecyloctadecanol, which has 24 carbon atoms, is a preferred Guerbet alcohol for use in the present invention.

Because $R^1$ is a hydrocarbon, the monoalcohol is a monofinctional reactant under the reaction conditions employed to prepare an ETDABP (as discussed later). Furthermore, under preferred reaction conditions, $R^1-OH$ is the only monofunctional reactant used to form the ETDABP. Thus, a reactant mixture useful in preparing ETDABP preferably does not contain monocarboxylic acid (ie., an organic molecule containing a single carboxylic acid group) and/or monoamine (i.e., an organic molecule containing a single amine group).

However, optional reactants may be employed to prepare an ETDABP gellant of the invention. For example, diacid other than dimer acid (ie., co-diacid) may be employed. In general, the diacid component of the ETDABP-forming reaction mixture may be represented by the formula HOOC—$R^2$—COOH, and may therefore be referred to as a dicarboxylic acid, a dibasic acid or a dibasic carboxylic acid. In general, $R^2$ is a hydrocarbon group where the carbon atoms thereof may be arranged in a linear, branched or cyclic fashion, and the group be saturated or unsaturated. In one embodiment of the invention, the diacid is exclusively polymerized fatty acid, as discussed above.

In another embodiment of the invention, the diacid used to prepare the ETDABP gellant is a mixture of polymerized fatty acid and "co-diacid," where the term co-diacid simply refers to any diacid of formula HOOC—$R^2$—COOH (where $R^2$ is defined above) excluding polymerized fatty acid. An exemplary co-diacid is a so-called "linear" diacid of the formula HOOC—$R^2$—COOH wherein $R^2$ is a linear $C_{4-12}$ hydrocarbon group, and more preferably is a linear $C_{6-8}$ hydrocarbon group. Linear diacids suitable for the present invention include 1,6-hexanedioic acid (adipic acid), 1,7-heptanedioic acid (pimelic acid), 1,8-octanedioic acid (suberic acid), 1,9-nonanedioic acid (azelaic acid), 1,10-decanedioic acid (sebacic acid), 1,11-undecanedoic acid, 1,12-dodecanedioic acid (1,10-decanedicarboxylic acid), 1,13-tridecanedioic acid (brassylic acid) and 1,14-tetradecanedioic acid (1,12-dodecanedicarboxylic acid).

Another exemplary co-diacid that may be used to prepare an ETDABP gellant is the reaction product of acrylic or methacrylic acid (or the ester thereof, with a subsequent hydrolysis step to form the acid) and an unsaturated fatty acid. For example, a $C_{21}$ diacid of this type may be formed by reacting acrylic acid with a $C_{18}$ unsaturated fatty acid (e.g., oleic acid), where an ene-reaction presumably occurs between the reactants. An exemplary $C_{21}$ diacid is commercially available from Westvaco Corporation, Chemical Division, Charleston Heights, S.C., as their product number 1550.

Aromatic diacids may be used as the co-diacid. An "aromatic diacid" as used herein is a molecule having two carboxylic acid groups (—COOH) or reactive equivalents thereof (e.g., acid chloride (—COCl) or ester (—COOR)) and at least one aromatic ring ("Ar"). Phthalic acids, e.g., isophthalic acid and terephthalic acid, are exemplary aromatic diacids. The aromatic diacid may contain aliphatic carbons bonded to the aromatic ring(s), as in HOOC—$CH_2$—Ar—$CH_2$—COOH and the like. The aromatic diacid may contain two aromatic rings, which may be joined together through one or more carbon bonds, (e.g., biphenyl with carboxylic acid substitution) or which may be fused (e.g., naphthalene with carboxylic acid substitution).

However, ETDABP gellants may also contain $R^2$ groups having less than 30 carbon atoms. For example, an ETDABP gellant of the invention may contain one or more $R^2$ groups having about 4 to 19, preferably about 4 to 12, and more preferably about 4 to 8 carbon atoms. The carbon atoms may be arranged in a linear, branched or cyclic fashion, and unsaturation may be present between any two carbon atoms. Thus, $R^2$ may be aliphatic or aromatic. When present, these lower carbon-number $R^2$ groups are preferably formed entirely of carbon and hydrogen, i.e., are hydrocarbon groups. Such lower carbon-number $R^2$ groups preferably constitute less than 50% of the $R_2$ groups; however, when present, constitute about 1% to about 50%, and preferably about 5% to about 35% of the total of the $R^2$ groups. The identity of $R^2$ at each occurrence is independent of the identity of $R^2$ at any other occurrence.

A preferred gellant of the invention, which is also a preferred ETDABP of the invention, is referred to herein as an ester-terminated polyamide, or ETPA. ETPA comprises molecules of the formula (1), wherein n, $R^1$, $R^2$ and $R^3$ are defined herein.

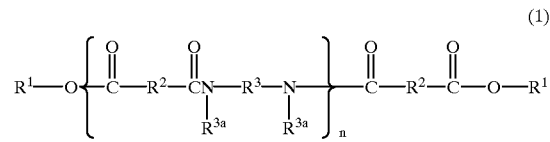

(1)

Thus, the invention is directed to gels formed, in part, of an ester-terminated polyamide of the formula (1) wherein n designates a number of repeating units such that ester groups constitute from 10% to 50% of the total of the ester and amide groups; $R^1$ at each occurrence is independently selected from an alkyl or alkenyl group containing at least 1 carbon atom, preferably at least 4 carbon atoms; $R^2$ at each occurrence is independently selected from a $C_{4-42}$ hydrocarbon group with the proviso that at least 50% of the $R^2$ groups have 30–42 carbon atoms; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen. For convenience, $R^1$, $R^2$, $R^3$ etc. will be referred to herein as "groups", however they could equally well be referred to as radicals ($R^1$) and diradicals ($R^2$ and $R_3$).

As may be seen from formula (1), the preferred ETPA gellants have ester groups, ie., —C(═O)O— groups (which may equally well be written as —OC(═O)— groups) at both ends of a series of amide groups, i.e., —N($R^{3a}$)C(═O)— groups (which may equally well be written as —C(═O)N($R^{3a}$)— groups). The letter "n" designates the number of repeating units present in a molecule of ETPA, and is an integer greater than 0. According to the invention, n may be 1, in which case the ETPA contains equal numbers of ester and amide groups, i.e., the ester groups constitute 50% of the total of the ester and amide groups in the ETPA molecule. The preferred ETPA gellants are of relatively low molecular weight, so that n is preferably 1 to about 10, and more preferably is 1 to about 5. Because the ETPA molecules have such a low molecular weight, they could equally well be referred to as ester-terminated oligoamides. In any event, viewed another way, the ester groups constitute about 10% to about 50%, preferably about 15% to about 40%, and more preferably about 20% to about 35% of the total of the ester and amide groups. A preferred ETPA gellant includes a mixture of ETPA molecules of formula (1) having various n values.

The $R^1$ group in formula (1) is an alkyl or alkenyl group which contains at least 1, and preferably at least 4 carbon atoms. Alkyl groups are preferred, however alkenyl groups having 1–3, and preferably 1 site of unsaturation are also suitable. When ETPA molecules are made wherein $R^1$ has 4 or less carbon atoms, the ETPA is a very poor gellant for pure hydrocarbon, particularly pure aliphatic hydrocarbon. Accordingly, ETPA gellants having formula (1) wherein $R^1$ is less than four are preferably used in preparing gels that are contained within a jar, rather than free-standing. Alternatively, the ETPA of formula (1) wherein $R^1$ is less than four might be used in combination with a gellant that provides a more rigid structure.

However, it has been surprisingly found that when the number of carbon atoms in the $R^1$ group is increased above 4, and preferably has at least about 10 carbon atoms, more preferably at least about 12 carbon atoms, then ETPA is an excellent gellant for aliphatic hydrocarbon. The upper range for the number of carbon atoms in the $R^1$ group is not particularly critical, however preferably the $R^1$ group has less than or equal to about 24 carbon atoms, and more preferably has less than or equal to 22 carbon atoms. $R^1$ groups having about 16–22 carbon atoms are highly preferred. The identity of $R^1$ at any occurrence is independent of the identity of $R^1$ at any other occurrence.

The $R^2$ group in formula (1) is suitably a hydrocarbon containing 4 to 42 carbon atoms. A preferred $R^2$ group contains 30–42 carbon atoms (ie., is a $C_{30-42}$ group), and at least 50% of the $R^2$ groups in an ETPA gellant preferably have 30–42 carbon atoms. Such $R^2$ groups are readily introduced into an ETPA when the gellant is prepared from polymerized fatty acid, also known as dimer acid. Polymerized fatty acid is typically a mixture of structures, where individual dimer acids may be saturated, unsaturated, cyclic, acyclic, etc. Thus, a detailed characterization of the structure of the $R^2$ groups is not readily available. However, good discussions of fatty acid polymerization may be found in, e.g., U.S. Pat. No. 3,157,681 and *Naval Stores—Production, Chemistry and Utilization*, D. F. Zinkel and J. Russel (eds.), Pulp. Chem. Assoc. Inc., 1989, Chapter 23.

Typical unsaturated fatty acids used to form polymerized fatty acid include oleic acid, linoleic acid, linolenic acid, etc. Tall oil fatty acid, which is a mixture containing long-chain unsaturated fatty acids obtained as a byproduct of the wood pulping process, is preferred for preparing polymerized fatty acid useful in ETPA formation. While tall oil fatty acid is a preferred source of long-chain fatty acid, the polymerized fatty acid may alternatively be prepared by polymerization of unsaturated fatty acids from other sources, e.g., soybeans or canola. The $R^2$ group containing 30–42 carbon atoms may thus be described as having the structure of dimer or trimer acid, after removal of the carboxylic acid groups (as seen below, the carboxylic acid groups of dimer acid can react to form the amide and/or ester groups of the ETPA gellant).

While the preferred ETPA gellants contain at least 50% $C_{30-42}$ groups as the $R^2$ group, more preferably the total of the $R^2$ groups consist of at least 75% $C_{30-42}$ groups, and still more preferably consist of at least 90% $C_{30-42}$ groups. ETPA gellants of formula (1) wherein $R^2$ is entirely $C_{30-42}$ are preferred gellants of the invention.

However, ETPA gellants may also contain $R^2$ groups having less than 30 carbon atoms. For example, an ETPA gellant may contain one or more $R^2$ groups having about 4 to 19, preferably about 4 to 12, and more preferably about 4 to 8 carbon atoms. The carbon atoms may be arranged in a linear, branched or cyclic fashion, and unsaturation may be present between any two carbon atoms. Thus, $R^2$ may be aliphatic or aromatic. When present, these lower carbon-number $R^2$ groups are preferably formed entirely of carbon and hydrogen, i.e., are hydrocarbon groups. Such lower carbon-number $R^2$ groups preferably constitute less than 50% of the $R_2$ groups; however, when present, constitute about 1% to about 50%, and preferably about 5% to about 35% of the total of the $R^2$ groups. The identity of $R^2$ at each occurrence is independent of the identity of $R^2$ at any other occurrence.

The $-N(R^{3a})-R^3-N(R^{3a})-$ group in formula (1) links two carbonyl (C=O) groups. In a preferred embodiment of the invention, all of the $R^{3a}$ groups in an ETPA gellant are hydrogen, so that $R^3$ alone joins the two nitrogen atoms shown in the formula $-N(R^{3a})-R^3-N(R^{3a})-$. In this case, the $R^3$ group contains at least two carbon atoms, and optionally oxygen and/or nitrogen atoms, in addition to any hydrogen atoms that are necessary to complete otherwise unfilled valencies of the carbon, oxygen and nitrogen atoms. In a preferred embodiment, $R^3$ is a hydrocarbon group, having 2 to about 36 carbon atoms, preferably having 2 to about 12 carbon atoms, and more preferably having 2 to about 8 carbon atoms. These carbon atoms may be arranged in a linear, branched or cyclic fashion, and unsaturation may be present between any two of the carbon atoms. Thus, $R^3$ may contain aliphatic or aromatic structures. The identities of $R^3$ and $R^{3a}$ at each occurrence are independent of their identities at any other occurrence.

The $R^3$ groups may contain oxygen and/or nitrogen in addition to carbon and hydrogen atoms. A typical oxygen atom-containing $R^3$ group is a polyalkylene oxide, i.e., a group having alternating alkylene groups and oxygen atoms. Indeed, the oxygenation in a $R^3$ group is preferably present as an ether group. Representative polyalkylene oxides include, without limitation, polyethylene oxide, polypropylene oxide and copolymers (either random, alternating or block) of ethylene oxide and propylene oxide. Such oxygenated $R^3$ groups are readily introduced into an ETPA molecule of the invention through use of Jeffamine™ diamines (Huntsman Chemical, Inc., Houston, Tex.). These materials are available in a wide range of molecular weights. While some of the $R^3$ groups may contain oxygen (at least about 1%), preferably a minor number (less than 50%) of the $R^3$ groups contain oxygen, and more preferably less than about 20% of the $R^3$ groups contain oxygen. The presence of oxygen-containing $R^3$ groups tends to lower the softening point of the ETPA.

When present, the nitrogen atoms in an $R^3$ group are preferably present as secondary or tertiary amines. A typical nitrogen atom-containing $R^3$ group having secondary amine groups is a polyalkylene amine, i.e., a group containing alternating alkylene groups and amine groups, which is sometimes referred to as a polyallylene polyamine. The alkylene group is preferably a lower alkylene group, e.g., methylene, ethylene, (ie., $-CH_2CH_2-$), propylene etc. A typical polyallylene amine may be represented by the formula $-NH-(CH_2CH_2NH)_mCH_2CH_2-NH-$ wherein m is an integer from 1 to about 5.

However, the nitrogen atoms in the nitrogen-containing $R^3$ group may alternatively (or additionally) be present as tertiary nitrogen atoms, e.g., they may be present in a heterocycle of the formula:

wherein $R_c$ is a $C_{1-3}$ alkyl group.

In the above-described nitrogen atom-containing $R^3$ groups, $R^{3a}$ was hydrogen. However, $R^{3a}$ is not limited to hydrogen. In fact, $R^{3a}$ may be a $C_{1-10}$alkyl group, preferably a $C_{1-5}$alkyl group, and more preferably a $C_{1-3}$alkyl group. In addition, $R^3$ and $R^{3a}$, or two $R^{3a}$ groups, may together form a heterocyclic structure, e.g., a piperazine structure such as

In this case, the two $R^{3a}$ groups may be seen as joining together to form an ethylene bridge between the two nitrogen atoms, while $R^3$ is also an ethylene bridge.

The ETPA gellant typically includes a mixture of ETPA molecules of formula (1) in addition to, for example, by-products that are formed during the ETPA-forming reaction. While the ETPA molecules of formula (1) may be purified from such by-products using, e.g., chromatography or distillation, the by-products are typically either minimal in amount or impart desirable properties to the gellant, and thus need not be separated from the molecules of formula (1) in order for a suitable ETPA gellant to be formed.

As described herein, alcohols, amines and carboxylic acids are preferred starting materials to form the ETDABP and ETPA gellants of the invention. These starting materials are preferably reacted together with a stoichiometry, and under reaction conditions, such that the acid number of the resulting gellant is less than 25, preferably less than 15, and more preferably less than 10, while the amine number is preferably less than 10, more preferably less than 5, and still more preferably less than 1. The softening point of the gellant is preferably greater than room temperature, more preferably is about 50° C. to about 150° C., and still more preferably is about 80° C. to about 130° C.

In the ETDABP-and ETPA-gellant forming reactions of the invention, some material of formula (1) wherein n=0, i e., diester, is typically be formed. Such a gellant could also be produced by preparing ETDABP as described above (having little or no n=0 material), and then preparing diester of formula (1) (n=0 exclusively, having no amide groups) in a separate reaction, and mixing the two materials together. However, diester alone is not a useful gellant, and thus the ETDABP- and ETPA-gellants preferably contain only small quantities of the diester, e.g., less than 10% by weight and more preferably even less.

It is important to control the stoichiometry of the reactants in order to prepare an ETPA gellant according to the invention. In the following discussion regarding reactant stoichiometry, the terms "equivalent(s)" and "equivalent percent" will be used, and are intended to have their standard meanings as employed in the art. However, for additional clarity, it is noted that equivalents refer to the number of reactive groups present in a molar quantity of a molecule, such that a mole of a dicarboxylic acid (e.g., sebacic acid) has two equivalents of carboxylic acid, while a mole of monoalcohol has one equivalent of hydroxyl. Furthermore, it is emphasized that the diacid has only two reactive groups (both carboxylic acids), the monoalcohol has only one reactive group (a hydroxyl group) and the diamine has only two reactive groups (preferably both primary amines), and these are preferably, although not necessarily, the only reactive materials present in the reaction mixture.

In preparing an ETPA gellant, the equivalents of carboxylic acid are substantially equal to the combined equivalents of hydroxyl contributed by monoalcohol and amine contributed by diamine. In other words, if the reaction mixture used to form an ETPA gellant has "x" equivalents of carboxylic acid, "y" equivalents of amine and "z" equivalents of hydroxyl, then $0.9 \leq \{x/(y+z)\} \leq 1.1$, and preferably $\{x/(y+z)\}$ is substantially 1.0. Under these conditions, substantially all of the carboxylic acid groups will react with substantially all of the hydroxyl and amine groups, so that the final product contains very little unreacted carboxylic acid, hydroxyl or amine groups. In other words, each of the acid and amine numbers of the gellant is preferably less than about 25, is more preferably less than about 15, and is still more preferably less than about 10, and is yet still more preferably less than about 5.

When co-diacid is employed to prepare an ETPA gellant, the co-diacid preferably contributes no more than about 50% of the equivalents of carboxylic acid present in the reaction mixture. Stated another way, the co-diacid contributes from 0–50 equivalent percent of the acid equivalents in the reaction mixture. Preferably, the co-diacid contributes 0–30 equivalent percent, and more preferably contributes 0–10 equivalent percent of the acid equivalents in the reaction mixture.

When co-diamine is employed to prepare an ETPA gellant, the co-diamine preferably contributes no more than about 50% of the equivalents of amine present in the reaction mixture. Stated another way, the co-diamine contributes from 0–50 equivalent percent of the amine equivalents in the reaction mixture. Preferably, the co-diamine contributes 0–30 equivalent percent, and more preferably contributes 0–10 equivalent percent of the amine equivalents in the reaction mixture.

In order to prepare the ETPA gellant, it is important to control the relative equivalents of hydroxyl and amine used in the gellant-forming reaction. Thus, hydroxyl groups contribute about 10–70% of the total equivalents of hydroxyl and amine employed to prepare the gellant. Stated another way, $0.1 \leq \{z/(y+z)\} < 0.7$, where y and z have been defined above. In a preferred embodiment, $0.2 \leq \{z/(y+z)\} \leq 0.5$, while in a further preferred embodiment, $0.25 \leq \{z/(y+z)\} \leq 0.4$.

The stoichiometry of the reactants will have a significant impact on the composition of the ETDABP and ETPA gellants. For example, ETDABP and ETPA gellants made with increasing amounts of monoalcohol will tend to have lower average molecular weights. In other words, as more monofunctional reactant is used, the number of amide pairs in an average molecule of formula (1) will decrease. In fact, when 70 equivalent percent monoalcohol is employed, the majority of the molecules of formula (1) in the gellant will have only one or two amide pairs. On the other hand, as less monoalcohol is used, the average molecular weight of the molecules in the ETDABP or ETPA gellant will increase. In general, increasing the average molecular weight of the ETDABP or ETPA components will tend to increase the melting point and melt viscosity of the gellant, which tends to provide a firmer gel when the gellant is combined with a low polarity liquid or other solvent.

In order to prepare an ETDABP gellant, the above-described reactants (diacid, diamine and monoalcohol or reactive equivalents thereof) may be combined in any order. Preferably, the reactants are simply mixed together and heated for a time and at a temperature sufficient to achieve essentially complete reaction, to thereby form the ETDABP gellant. During formation of the ETDABP gellant, the diacid and diamine groups will alternate to form what may be termed an alternating copoylmer. Neither ETDABP nor ETPA is a block copolymer. The terms "complete reaction" and "reaction equilibrium" as used herein have essentially the same meaning, which is that further heating of the product gellant does not result in any appreciable change in the performance characteristics of the product gellant, where the most relevant performance characteristic is the ability of the product gellant to form a clear, firm gel upon being combined with a solvent.

Thus, the ETDABP gellant may be formed in a one-step procedure, wherein all of the monoalcohol, diacid (including co-diacid) and diamine (including co-diamine) are combined and then heated to about 200–250° C. for a few hours, typically 2–8 hours. Since one or more of the reactants may be a solid at room temperature, it may be convenient to combine each of the ingredients at a slightly elevated temperature, and then form a homogeneous mixture prior to heating the reaction mixture to a temperature sufficient to cause reaction between the monoalcohol, diacid and diamine. Alternatively, although less preferably, two of the reactants may be combined and reacted together, and then the third reactant is added followed by further heating until the desired product is obtained. Reaction progress may be conveniently monitored by periodically measuring the acid and/or amine number of the product mixture.

As one example, the diacid may be reacted with the diamine so as to form polyamide, and then this intermediate polyamide may be reacted with monoalcohol to form ester-terminated dimer acid-based polyamide. Or, the diacid may be reacted with the monoalcohol to thereby form diester, and this diester may be reacted with diamine to thereby form ester-terminated dimer acid-based polyamide. Because the components of the product gellant are preferably in reaction equilibrium (due to transamidation and transesterification reactions), the order in which the reactants are combined preferably does not impact on the properties of the gellant.

Any catalyst that may accelerate amide formation between carboxylic acid and amine groups, and/or ester formation between carboxylic acid and hydroxyl groups, may be present in the reaction mixture described above. Thus, mineral acid such as phosphoric acid, or tin salts such as dibutyltin oxide, may be present during the reaction. In addition, it is preferred to remove water from the reaction mixture as it is formed upon amide and ester formation. This is preferably accomplished by maintaining a vacuum on the reacting mixture.

The gels of the invention are formed from components including at least one each of a gellant and a solvent, where a preferred gellant is ETDABP as described above. The gels may be formulated to function as a candle or other article which will be intentionally burned, in which case the solvent is preferably flammable. Whether or not the gel is flammable or is intended to be burned, it may contain various active ingredients which may be emitted from the gel. For instance, a fragrance may be a component of the gel, where the fragrance may be the, or one of the solvents which forms a gel with ETDABP. Thus, the solvent is an important component of the gel, and will be described next. In general, the solvent is preferably non-aqueous, in that it does not contain any appreciable amount of water. This is true regardless of whether the article is intended to be flammable, e.g., a candle or fuel, or is intended as a controlled-release device, e.g., an air freshener.

When a gel is formulated with the intention that the gel-containing article will be burned, the solvent is preferably flammable. Thus, the gel preferably does not contain appreciable moisture when the gel is intended to be a component in an article which should be burned. A flammable solvent for preparing gels of the invention typically has a flash point ranging from about –15° C. to about 300° C., and preferably from about –15° C. to about 225° C. When the article is primarily intended to be a fuel source, L.e., is intended to be used to assist the lighting of a fire in a fireplace, a campfire, a charcoal fire, etc., then the flash point of the solvent preferably ranges from about –15° C. (e.g., hexane) to about 225° C. (e.g., heavy mineral oil). A preferred flash point is between about 40° C. and about 90° C. When the article is primarily intended to be a candle, i e., primarily for decorative purposes and home use, then the flash point of the solvent should be about 130° C. to about 225° C., and is preferably about 150° C. to about 200° C. Candles, more than fuel sources, are intended for slow burning and may be left unobserved for periods of time. For these reasons, a higher flash point is generally preferred for a candle compared to a fuel source, so that the candle burns more slowly and safely.

Methods to measure flash point are well known. For example, ASTM D-92 and D-93 provide procedures for determining the flash point of a solvent. The current address for ASTM is 100 Barr Harbor Drive, West Conshohocken Pa. 19428-2959. ASTM D92-90 (i.e., test D92, last revised in 1990) as set forth in the Annual Book of ASTM Standards, Section 5 (pages 28–32 in 1996 edition), is directed to a test method for measuring flash and fire points by the so-called Cleveland Open Cup method. The Cleveland Open Cup method is particularly suited for measuring the flash points of viscous materials having a flash point of 79° C. and above, i.e., liquids with relatively high flash points such as mineral oils. ASTM D93-94 as set forth in the Annual Book of ASTM Standards, Section 5 (pages 33–46 is 1996 edition), is directed to a test method for measuring flashpoint by the Pensky-Martens Closed Cup Tester. The Pensky-Martens Closed Cup Tester may be used with fuel oils, lubricating oils, and other homogeneous liquids. VWR Scientific Products, having a website at http://www.vwrrsp.com, presently sells a Pensky-Martens Flash Point Tester, Electric Boekel; a Pensky-Martens Flash Point Tester, Precision; and a Tag Closed Cup Flash Tester, Koehler, any of which may be used to determine flash points according to the present invention.

While flash point may be measured by the above-listed techniques, in addition, many reference books and catalogs provide flash point information about solvents and fuels. For example, the Aldrich Chemical Company (Milwaukee, Wis.) offers a catalog of over a thousand chemicals, and in this catalog the flash points of many of the available chemicals is set forth. The Material Data Safety Sheet (MSDS) that is often available from a chemical manufacture, typically provides flash point information about the chemical.

The solvent may be a liquid or solid at room temperature, but is preferably a liquid. Examples of solvents that are solid at room temperature include fatty acids and fatty alcohols, such as myristic acid (flash point >159° C.) and myristyl alcohol (flash point >143° C.). The solvent is preferably a liquid at a temperature between 10–60° C.

A preferred solvent is a low polarity liquid, while a preferred low polarity liquid is a hydrocarbon, and preferred hydrocarbons are oils. As used herein, the term solvent includes any substance which is a liquid at a temperature between 10–60° C., and which forms a gel upon being combined with a gellant. The prior art sometimes distinguishes solvents and oils in that defatting occurs when solvents are rubbed on human skin, leading to drying and irritation, however, defatting does not occur when oils are rubbed on human skin. As used herein, the term solvent will be used to encompass oils and other fluids which may be gelled, and is not limited to liquids that cause defatting of human skin.

Many different oils may be used as solvents in the present invention, including vegetable oil, animal oil and mineral oil. However a preferred oil is mineral oil, also sometimes referred to as medicinal oil. Mineral oil is a highly refined, colorless, tasteless, and odorless petroleum oil (i.e., derived by processing petroleum/crude oil) used medicinally as an internal lubricant and for the manufacture of salves and ointments. Such mineral oils are highly refined in having substantially all volatile hydrocarbons removed therefrom, and in being hydrogenated (also called hydrotreated) in order to remove substantially all unsaturation, e.g., aromatic groups have been reduced to the fully saturated analog. A preferred mineral oil to prepare a gel of the invention is so-called "white" mineral oil, which is water-white (i.e., colorless and transparent) and is generally recognized as safe for contact with human skin. Mineral oil may also be characterized in terms of its viscosity, where light mineral oil is relatively less viscous than heavy mineral oil, and these terms are defined more specifically in the U.S. Pharmacopoeia, $22^{nd}$ revision, p. 899 (1990).

Any mineral oil may be used in the invention as a solvent to form a gel. Mineral oils are available commercially in both USP and NF grades. USP mineral oils have viscosities that range from 35 cSt to 100 cSt, and pour points that range from −40° C. to −12° C. NF light mineral oils have lower viscosities, typically 3–30 cSt, and pour points as low as −45° C. The mineral oil may be of technical grade, having a viscosity ranging from 4–90 cSt and a pour point ranging from −12° C. to 2° C.

Examples of suitable, commercially available mineral oils include Sonneborn® and Carnation® white oils from Witco, Isopar® K and Isopar® H from Exxon, and Drakeol® and Peneteck® white mineral oils from Penreco.

Other hydrocarbon solvents that may be used in the invention include relatively lower molecular weight hydrocarbons including linear saturated hydrocarbons such a tetradecane, hexadecane, octadecane, etc. Cyclic hydrocarbons such as decahydronaphthalene (DECALIN), fuel grade hydrocarbons, branched chain hydrocarbons such as PERMETHYL from Permethyl Corporation and ISOPAR from Exxon Corp., and hydrocarbon mixtures such as product PD-23 from Witco (Greenwich, Conn.) may also be used in preparing gels of the invention. Such hydrocarbons, particularly saturated hydrocarbon oils, are a preferred solvent for preparing a gel of the invention.

Another class of suitable low polarity liquid solvents is esters, and particularly esters of fatty acids. Such esters may be monofunctional esters (i.e., have a single ester moiety) or may be polyfunctional (i.e., have more than one ester group). Suitable esters include, but are not limited to, the reaction products of $C_{1-24}$ monoalcohols with $C_{1-22}$ monocarboxylic acids, where the carbon atoms may be arranged in a linear, branched and/or cyclic fashion, and unsaturation may optionally be present between carbon atoms. Preferably, the ester has at least about 18 carbon atoms. Examples include, but are not limited to, fatty acid esters such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate and tetratriacontanyl stearate; salicylates, e.g. $C_{1-10}$ salicylates such as octyl salicylate, and benzoate esters including $C_{12-15}$ alkyl benzoate, isostearyl benzoate and benzyl benzoate.

Suitable esters include glyceryl and propylene glycol esters of fatty acids, including the so-called polyglycerol fatty acid esters and triglycerides. Exemplary esters include, without limitation, propylene glycol monolaurate, polyethylene glycol (400) monolaurate, castor oil, triglyceryl diisostearate and lauryl lactate. Thus, the solvent may have more than one of ester, hydroxyl and ether functionality. For example, $C_{10-15}$ alkyl lactate may be used in forming a gel of the invention. In addition, esterified polyols such as the polymers and/or copolymers of ethylene oxide, propylene oxide and butylene oxide reacted with $C_{1-22}$ monocarboxylic acids are useful. The carbon atoms of the $C_{1-22}$ monocarboxylic acids may be arranged in a linear, branched and/or cyclic fashion, and unsaturation may be present between the carbon atoms. Preferred esters are the reaction product of an alcohol and a fatty acid, where the alcohol is selected from $C_{1-10}$ monohydric alcohol, $C_{2-10}$ dihydric alcohol and $C_{3-10}$ trihydric alcohol, and the fatty acid is selected from a $C_{8-24}$ fatty acid. Two triglyceride esters that are commercially available and may be used as a solvent in the present invention are Softigen® from Hüls America of Piscataway, N.J. (a $C_{10}$–$C_{18}$ triglyceride), and Neobee® M5 from Stepan Chemical of Northfield, Ill. (a liquid capric/caprylic triglyceride).

In order to prepare a gel from ETDABP or ETPA and a solvent, the two components are mixed together and heated until homogeneous. A temperature within the range of about 80–150° C. is typically sufficient to allow the gellant to completely dissolve in the solvent. A lower temperature may be used if a solution can be prepared at the lower temperature. Upon cooling, the mixture forms the gel of the invention.

A precise definition of "gel" is not easy to give, although most if not all researchers recognize a "gel." Generally, a gel is more viscous than a liquid or paste, and retains its shape when left undisturbed, i.e., is self-supporting. However, a gel is typically not as hard or firm as a wax. Gels may be penetrated more easily than a wax-like solid, where "hard" gels are relatively more resistant to penetration than "soft" gels. A rigid gel as defined herein resists deformation upon the application of a force.

Almdale et al. (*Polymer Gels and Networks*, Vol. 1, No. 5 (1993)) list two criteria for defining a system as a gel: (1) a gel consists of two or more components, one of which is a liquid, present in substantial quantities; and (2) a gel is a soft material which is solid or solid-like. The solvents described herein include the liquid of Almdale. Whether Almdale's "soft material" is a gel can be described more accurately through rheological measurement. Typically, gels possess a storage modulus G' (w) which exhibits a pronounced plateau at higher frequencies (on the order of 1–100 radians/second), and a loss modulus G" (w) which is considerably smaller than the storage modulus in the plateau region. In a strict sense, the term "gel" applies to systems having a value G' (w) that is higher than its value of G" (w) at low frequencies. Many of the compositions according to the present invention are gels by one or both of the above definitions. A gel is free-standing or self-supporting in that its yield value is greater than the shear stress imposed by gravity.

Rheological parameters such as the storage modulus G' (w) can be measured as a function of angular frequency with a parallel-plate rheometer. For example, such parameters can be generated using a Rheometrics Dynamic Analyzer Model 70, using a 0.5 cm stainless steel plate and a 2.3 mm sample gap, over a temperature sweep of 25–85° C. at 1% strain and 6.3 radians/sec. A characterization of the rheological behavior of a gelled body according to the present invention was made using the Rheometrics instrument and conditions set forth above. The gel was prepared according to Example 3 set forth herein. As demonstrated by FIG. 1, the elastic modulus (G') is 5–10 fold greater than the loss modulus (G") at room temperature for this composition, thus demonstrating that a gel structure is present. As the gel is heated, it retains significant gel-like character at least up to about 50° C. However, as the gel is further heated, and the melting point of the ETDABP gellant is reached, the loss modulus will eventually equal the storage modulus (i.e., tan δ equals 1), and the composition loses its gel-like character (at a temperature of about 65–70° C., based on extrapolation of the data in FIG. 1).

Preferably, the solvent is a low-polarity liquid as described above, and more preferably the solvent is a liquid hydrocarbon. The liquid may contain more than one component, e.g., hydrocarbon as well as ester-containing material. In the mixture, the gellant (e.g., ETDABP) contributes 10–95%, and the solvent contributes 5–90% of the combined weight of the gellant and the solvent Preferably, the gellant is combined with the solvent such that the weight percent of gellant in the gellant +solvent mixture is about 5–50%, and preferably is about 10–45%. Such gels may be transparent, translucent or opaque, depending on the precise identities of the gellant and solvent, as well as the concentration of gellant in the mixture.

After the molten homogeneous mixture of gellant and solvent has been formed, it is allowed to cool, whereupon it forms a gel. The gel may be used as a candle or fuel, however when it is intended that the gel be burned, the gel preferably does not contain an appreciable amount of moisture, ie., the gel is preferably non-aqueous. Thus, solvents of the present invention are preferably substantially moisture-free, i.e., are non-aqueous.

A gel formed from ETDABP or ETPA may adhere to the sides of the container in which the gel is formed. During cooling, the molten homogeneous mixture will undergo some contraction, which may be impeded if the gel sticks to the sidewalls of the container. In these instances, cracks may form in the cooling gel, because the contracting gel is adhering to the container. When a crack-free candle or other article is desired, such a product may be prepared by allowing the gel to cool to just above its gel point, and then pouring the cooled gel into a mold. In this way, the degree of cooling, and hence contraction, that occurs within the mold is minimized, with concomitant reduction in cracking.

If desired, the molten mixture may be poured into a mold or a jar, and the mixture cooled therein to form the candle or fuel. The mold may be used when the gel desirably has an ornamental exterior surface. For example, the mold may impart various designs, in a relief fashion, to the surface of the gel. A preferred design is a ridged pattern, with the ridges preferably extending vertically (from top to bottom) along the sides of the candle. These ridges are desirable because they minimize the surface area which is contacted when a person picks up the candle, and therefore there is less opportunity for smudges and fingerprints to be imparted to the surface of the candle.

Molds to achieve various relief surfaces are commonly used in the preparation of paraffin-based candles, and are well known in the art. A pillar shape, which is a common and desired form for candles, is a preferred shape for the gel. Cubes and cylinders are other suitable shapes for the gel. An appropriate quantity of mold-release agent may be placed on the interior mold surface, in order to facilitate removal of the gel from the mold. Such mold-release agents may contain silicon or fluorocarbon, are available from many commercial sources, and are known in the art.

Alternatively, the molten mixture may be poured into a jar or like container, to permanently hold the gel. The jar may be formed of clear or colored glass, and have essentially any shape, according to the aesthetic preferences of the manufacturer. Alternatively, the jar may be formed of any other non-flammable substance, e.g., metal. A noteworthy feature of the ETDABP gels of the invention is their transparent and colorless appearance, and thus containers which allow the consumer to appreciate this appearance, e.g., clear glass or mirrored surface jars, are preferred. However, when the gel will be used primarily as a fuel source during, for example, camping, the container is preferably robust and not easily broken. For these instances, the container is preferably metal, e.g., aluminum or the like. Essentially the same procedures and considerations are relevant when preparing a non-flammable gel of the invention, which is intended primarily as a controlled release composition to release fragrance or anti-insect chemicals.

Regardless of whether the molten mixture is cooled in a mold or a jar, various decorative items may be placed within the mixture to enhance the appearance thereof. Such decorative items include so-called botanicals, which manufacturers currently place just below the surface of a paraffin candle, in order that the shadow of a leaf or otherwise shaped article can be seen on the candle's surface. Because the candles of the present invention may be transparent, such botanicals may be placed anywhere within the candle, to provide for a pleasing appearance. As another example, colored paraffin beads, or otherwise shaped items, may be added to the molten mixture at an appropriate time during its cooling, so that the decorative items are suspended in the gel. As yet another example, colorant may be gently stirred into the otherwise clear, cooling molten mixture, so that coloration in a swirling pattern may be seen in the final gel. The botanicals, beads or other decorative items should be added to the cooling molten mixture at a time when the viscosity of the molten mixture is such that the decorative items will not simply sink to the bottom of the mold or jar. This time will depend on the exact identity of the decorative items, and can be readily determined by the skilled artisan without undue experimentation.

When a wick is positioned in a flammable gel as described herein, a candle is formed. Such a candle has a surface which is preferably free of bubbles, cracks, chips, etc., when seen by the unaided eye. The candle may be transparent, translucent or opaque, and may be colorless, white or any other color, if dyes or pigments are added to the formulation. The candle preferably contains a single wick, where the wick is preferably positioned in the center of the candle. Alternatively, the candle may have a plurality of wicks. Upon burning, the candle preferably displays a bright, calm flame, and gradually forms a pool surrounding the so-called cup rim.

Candle wicks are commercially available, and the precise wick should be selected, in part, based on the size of the candle. A preferred wick is made from uniform, tear-resistant cotton yarn made of medium- and long-stapled cotton which is seasoned and does not have moisture damage. A typical wick has from 15–42 strands (plys). A larger wick (more strands) is preferred for a larger candle. A transparent wick is preferably used, so that the entire candle (wick plus fuel, and coating is present) may be transparent. The wick should be free of contaminants which impair a suction effect needed for desirable burning. The wick should not leave ashes upon burning, and it should burn without visible release of soot. A preferred wick has an upright posture upon exiting the candle, with a slight curvature and formation of a glow point at the wick tip upon burning. The wick in a preferred candle has a medium curvature while the candle burns, and the flame burns without visible release of soot. There is preferably a slight afterglow formed immediately after the candle has been extinguished.

The wick may be embedded with wax or other additive which facilitates or provides desired burning properties. For example, the wick may be colored using a water or alcohol soluble dye. Examples of water and alcohol soluble dyes that may be used to color the wick include, without limitation, F,D&C Blue #1, D&C Orange #4, Ext D&C Violet #2, F,D&C Red #4, D&C Red #33, F,D&C Red #40, D&C Green #8, D&C Yellow #10, F,D&C Yellow #5 and D&C Green #5.

When the gelled body is to be used primarily as a fuel source, e.g., to maintain heat in a warmed tray of food, or to start a campfire, etc., the gelled body does not necessarily contain a wick. In general, the concentration of ETDABP can be 1–95 wt. % of the total weight of the gelled body. A preferred composition is 1–20 wt. % ETPA, 80–99 wt. % mineral oil (preferably with a flash point of 100–200° C.) and 0–10 wt. % fragrance, where the wt. % values are based on the total weight of the gelled body. As stated above, ISOPAR K and ISOPAR H (Exxon Chemicals, Houston, are preferred solvents for the gelled article intended as a heat source.

When preparing a candle or fuel, other optional ingredients, such as colorant, fragrance, insect repellent, insecticide, and/or preservative (for example, antioxidant and/or UV-inhibitors), may be added at any time prior to formation of the gel structure. For example, they may be added after the gellant and solvent have formed a homogeneous mixture. Alternatively, they may be added prior to the formation of a homogeneous mixture.

The preservative, which may be an antioxidant and/or a UV-inhibitor, should be present in an amount effective to achieve its or their desired purposes. Typically, at least about 0.1 wt. % of one or both of an antioxidant and UV inhibitor will be present in an article of the invention. Suitable antioxidants and UV-inhibitors are well known in the art, and include, without limitation, hydroxyditoluene, stearic hydrazide, 2,6-di-tert-butyl-4-methylphenol (BHT, an antioxidant), Irganox® 1010 hindered phenol antioxidant from Ciba-Geigy (Hawthorne, N.Y.) and Uvinul® 3206 UV-ihhibitor from BASF, Parsippany, N.J.

The colorant may, for example, be a pigment or a dye, however a dye is preferred for providing transparent articles. Dyes that are oil soluble are particularly well suited. Oil soluble dyes are well known in the art, and may be obtained from, for example, Pylam Products, Tempe Ariz. Pylam Products sells the following oil soluble dyes: D&C violet #2, D&C yellow #11, D&C green #6, D&C red #17, Pylakrome™ Red, Pylakrome™ brilliant blue, Pyla-Wax™ brilliant blue, Pyla-Wax™ canary yellow, Pyla-Wax™ violet A, and Pyla-Wax™ brilliant red, among others.

The amount of dye which should be present in the gel will depend on the intensity of the dye and the desired strength of the coloration of the gel. This amount can be readily determined by the skilled artisan, with little or no experimentation. Typically, a colorant amount of less than 1 wt. % (based on the total weight of the gel) is satisfactory, and often an amount of less than 0.5 wt. % or less than 0.25 wt. % is satisfactory. The colorant may be mixed together with the solvent and gellant at any time prior to, or during, formation of the gel.

Another optional ingredient is a fragrance. The term "fragrance" is intended to refer to a chemical or blend of chemicals that together have a desirable odor. Fragrances, therefore, typically consist of a blend of chemicals, fragrant chemicals or fragrance materials. A large number of fragrance materials are known and used in various products such as perfumes, cosmetics, soaps, detergents, etc. Any of the fragrance materials used in these products may be added to a gel of the present invention. Bush Boake Allen of Montvale, N.J. sells a large number of fragrance raw materials, some of which have been evaluated for use in gels of the present invention as set forth in Example 35 herein. The vast majority of the fragrance materials disclosed in Example 35 are themselves solvents, and have a flash point between −15° C. and +300° C. Furthermore, most if not all of these fragrance materials of Example 35 are compatible with the gels of the invention. These fragrance raw materials may be combined in numerous ways to create pleasing fragrances for candles and other compositions disclosed herein.

The amount of fragrance which should be present in the gel will depend on the intensity of the fragrance and the degree to which it is desired that the gel emit fragrance. This amount can be readily determined by the skilled artisan, with little or no experimentation. An amount of fragrance equal to at least about 0.1 wt. %, based on the total weight of the composition, is typically necessary in order to achieve at least some fragrance-emitting character for the composition. Typically, a fragrance amount of less than 50 wt. % (based on the total weight of the gelled body) is satisfactory, and often an amount of less than 20 wt. % or even less than 15 wt. % is satisfactory. In a typical gel having fragrance, the fragrance constitutes 1–5 wt. % of the total weight of the gel. The amount of fragrance in a candle may depend upon the presence of other optional ingredients. For example, when insect repellent is present in the candle, the fragrance concentration is typically less than 30 wt. % of the total weight of the gel, and preferably is 1–5 wt. %.

The fragrance may be mixed together with the solvent and gellant at any time prior to formation of the gel. However since many fragrance materials are rather volatile, it is preferred to add the fragrance to the ungelled composition at a relatively low temperature rather than a higher temperature. A temperature of about 80° C. is typically suitable for adding the fragrance to the gel.

Another optional ingredient is an insect repellent. Suitable insect repellents include, without limitation, citronella, DEET, terpineol, and benzalacetone. In a typical gel, the insect repellent constitutes about 0.1–20 wt. %, preferably 5–10 wt. % of the total weight of the gel. When a candle contains insect repellent, the preferred gellant concentration is 30–60 wt. % when the candle is in pillar form and 20–30 wt. % when the candle is non-pillar (ie., placed within a jar or the like). In preparing a candle that contains insect repellent, ETPA is a preferred gellant.

A preferred article of the invention contains 30–60% ETDABP, 40–70%, solvent, less than 50% fragrance (but at least about 0.1%) and less than 5% colorant (but at least about 0.25%), where these percentage values are weight percents based on the combined weight of the ETDABP, solvent, fragrance and colorant. Another preferred article contains 10–30% ETDABP, 65–80% solvent, less than 50% fragrance (but at least an effective amount) and less than 1% colorant (but at least an effective amount) where these percentage values are weight percents based on the combined weight of the ETDABP, solvent, fragrance and colorant.

One aspect of the present invention provides a gelled article which is not primarily intended to be flammable, but rather is intended to release an active ingredient. Thus, this aspect of the invention provides for a gelled composition that emits or otherwise makes available to its surrounding environment one or more active components of the gelled composition. Illustrative active components are fragrance materials and insecticides. This aspect of the invention provides for air fresheners, fragrance sticks, fragranced soft gels, insect repellents, insecticides and the like. For convenience, these compositions will be generally referred to herein as controlled release compositions. The active ingredients should be somewhat volatile in order to be emitted and released from the gel. However, the active ingredient may become volatile under the conditions of use for the article. That is, if the article is intended to be burned, as for example a candle or fuel, then the active ingredient may become volatile under the elevated temperature environment caused by the burning, however it is not particularly volatile at room temperature when the article is not being burned. Also, an active ingredient may be emitted in that it migrates to the surface of the gel and then comes into contact with the envirnoment.

The active component may be a fragrance material. Suitable fragrance materials include fine perfumes and commodity fragrance materials, where a large number of suitable fragrance materials are identified in Example 35 herein. It has been surprisingly discovered that fragrance materials can be combined with an ester-terminated dimer acid-based polyamide (and preferably with ETPA as defined above) to form a composition that not only emits fragrance, but is also homogeneous. An inhomogeneous composition is not desired because such compositions tend to have erratic fragrance release profiles, ie., they emit bursts of fragrance followed by periods of little or no fragrance release. The fragrance-containing compositions of the present invention provide for a controlled release of fragrance, i.e., a steady release of fragrance which lasts for a long time.

In addition, all or nearly all of the fragrance in the inventive compositions can be released from the composition. This is highly desirable and advantageous in comparison to some prior art compositions which, in contrast, hold some of the fragrance material and never allow it to be released into the environment.

When the fragrance material is a fine fragrance, the gelled composition is preferably in the form of a stick, which can be rubbed onto a surface to provide a layer of fragrance-releasing material. Such a composition will be referred to herein as a fragrance stick. Alternatively, the gelled composition may be a "soft gel" by which is meant a composition of gelatin-like consistency. A soft gel does not typically hold its structure under stress, and thus is preferably contained within a jar or the like. A soft gel may be applied to the skin or other surface by immersing a finger into the gel and then rubbing the residue from the finger onto another area of the skin. The term "fine fragrance" generally refers to fragrances which are used in fine (e.g. expensive) perfumes. ETDABP and ETPA are both well suited for use in fragranced sticks and soft gels because, not only can they form a stick-like consistency with fragrance and optional ingredients, the EPDABP and EPTA are not harmful or irritating to most surfaces, e.g., human skin.

In a typical fragranced stick or soft gel of the invention, the fine fragrance is present at a concentration within the range of about 1–50 wt. % of the composition, and preferably constitutes about 2–25 wt. % of the composition. The ETDABP or ETPA is present at a concentration within the range of about 5–50 wt. % of the composition, and is preferably present within the range of about 10–20 wt. %. Greater or lesser amounts of these components may be present, depending on the desired consistency of the stick and the compatibility of the fragrance with the ETDABP or ETPA.

Optional components may be present in the fragranced stick or soft gel. For example, a colorant may be present to impart desired coloration to the product. A preferred fragranced stick or gel, absent the colorant, is clear and transparent, although the fragranced stick or soft gel of the present invention may be opaque or translucent. In any event, the addition of colorant may enhance the visual appeal of the fragranced stick or gel, and the residue provided when the stick or gel is rubbed across a surface. The colorant may be a dye or a pigment, and is preferably non-irritating to the skin. Such colorants are well known in the art, and are used in, for example, lipsticks and eye shadow.

When present, the colorant is typically needed in only small amounts, for example, less than 5 wt. %, and often as little of 1 wt. % or even 0.1 wt. % is sufficient to impart a desired coloration to the fragrance stick. If a more intense coloration is desired, then the amount of colorant in the stick may be increased.

Another optional component is a volatile hydrocarbon. The addition of the volatile hydrocarbon may enhance the processing of the fragranced stick or soft gel. In other words, the volatile hydrocarbon may facilitate formation of a homogeneous mixture between the ETDABP or ETPA gellant and the fine fragrance. In addition, the volatile hydrocarbon will typically influence the consistency of the fragranced stick or gel, and can be used to impart enhanced delivery properties to the stick or gel. For instance, the incorporation of volatile hydrocarbon has been found to allow a convenient delivery of a thin layer of fragrant gel to the skin, with the absence of a concomitant wet residue that might otherwise be present.

The volatile hydrocarbon typically is a $C_{10}$–$C_{18}$ chemical formed entirely of carbon and hydrogen, where the carbon atoms may be arranged in a linear, branched or cyclic structure, and where unsaturation may be present between any two carbon atoms. Suitable volatile hydrocarbons include $C_{11}$–$C_{15}$ paraffinic and isoparaffinic compounds, including mixtures thereof. Exxon Chemicals (Houston, Tex.) sells suitable volatile hydrocarbons under their Isopar® L and Isopar® M trademarks. The volatile hydrocarbon is preferably odorless, and has only a slight vapor pressure.

When present, the volatile hydrocarbon constitutes about 5–90 wt. % of the fragranced stick or gel, and preferably constitutes about 10–50 wt. %. The amount of volatile hydrocarbon in the fragrance stick may be higher or lower than these typical ranges, depending on the desired consistency of the stick, the precise chemical composition of the volatile hydrocarbon, ETDABP or ETPA, and fine fragrance, and the presence of other optional components.

Another suitable optional component is a mineral oil. The mineral oil may be used to increase the pay-off of the fragranced stick or gel. The term "pay-off" refers to the amount of residue that is delivered to a surface when the fragranced stick, or a finger having a residue of soft gel, is rubbed across that surface under a typical pressure. Thus, the ideal fragranced stick or soft gel should have a pay-off which is neither too little nor too great. The pay-off of a stick or gel can typically be increased by increasing the amount of mineral oil in the composition. However, if too much mineral oil is present, then the composition provides an unpleasant greasy feel to the residue. The combination of mineral oil with volatile hydrocarbon may be used to provide desirable rub-off and non-greasy feel to fragranced sticks and gels of the present invention, and is a preferred combination that may be gelled with ETDABPA or ETPA according to the invention.

Another ingredient which may be used to increase the pay-off of the fragranced stick or gel is a fatty ester. The fatty ester may also be serve to prevent drying of the skin which is contacted with the fatty ester-containing gel of the invention. Such fatty esters are commonly used in skin lotions and the like, and thus are known to those of skill in the art. Suitable fatty esters include the esters of $C_{10}$–$C_{22}$ fatty acids and mono- or poly-hydric alcohols. Exemplary fatty acids include, without limitation, myristic acid, sebacic acid, oleic acid, palmitic acid and the like, and exemplary mono- and poly-hydric alcohols include, without limitation, $C_1$–$C_{22}$ monohydric alcohols such as methanol, 2-ethylhexanol, decanol, and hexadecanol, $C_2$–$C_{22}$ dihydric alcohols such as ethylene glycol, polyethylene glycol, neopentyl glycol, and $C_3$–$C_{22}$ trihydric alcohols such as glycerol.

The air freshener of this invention is prepared from components that include an ester-terminated dimer acid-based polyamide (ETDABP) and a fragrance, where ETPA is a preferred ETDABP. A typical inventive air freshener contains ETDABP in a concentration range of about 5–60 wt. %, and fragrance in a concentration range of about 1–50 wt. %, where these weight percent values are based on the total weight of the air freshener. The amounts of ETDABP and fragrance present in the air freshener can be varied outside these typical ranges, and still provide a useful product. The precise amounts of ETDABP and fragrance to be used in preparing an air freshener will depend on the qualities of the particular ETDABP and fragrance, as well as the desired consistency and other properties of the product.

ETDABP and fragrance may be combined according to the invention to provide a gel structure. Such a structure is desirable in that it provides for a sustained and controlled release of fragrance from the mixture. In general, the gel structure becomes firmer as the concentration of ETDABP increases in the air freshener, and can even adopt a "stick" type consistency, which refers to a very firm gel. The combination of ETDABP and fragrance can afford a clear or transparent structure. Such a transparent structure may increase the aesthetic appeal and application areas of the freshener in the marketplace.

Optional materials may be added to the air freshener. A suitable optional component is a colorant. The addition of colorant imparts coloration to the air freshener, and may thereby enhance the aesthetic appeal of the product. Any dye or pigment as discussed above may be used as the colorant.

Another optional component is a volatile hydrocarbon. The addition of volatile hydrocarbon is often desirable because it contributes to improved processing, in other words, the volatile hydrocarbon may facilitate the formation of a homogeneous gel structure. When present, the volatile hydrocarbon typically constitutes about 15–95% of the total weight of the air freshener.

The fragrance material preferably has low polarity. Highly polar fragrance materials are not preferred because they tend to be marginally compatible with the ETDABP or ETPA gellant, and accordingly cannot be formed into homogeneous gels having a high content of fragrance material. Typically, a high fragrance content is desirable for an air freshener, because such an air freshener may potentially have a longer useful lifetime. Air fresheners containing ETDABP or ETPA can typically be formulated to have higher amounts of non-polar fragrance materials than polar fragrance materials. However, the invention includes air fresheners which incorporate fragrance material having a wide range of polarities, including mixtures of fragrance materials of any polarity.

Another active substance which may be incorporated into a gel of the invention is an anti-insect chemical. The term "anti-insect chemical" is intended to encompass materials that are toxic and/or repugnant to an insect. The gel preferably has the consistency of a stick, or at least a firm gel, and will be referred to herein for convenience as an insect stick. The insect stick of the invention may be used to impart an anti-insect residue, in the form of a thin film, to a surface. Such a residue may be placed onto the surface of a cupboard, for example, in order to kill and/or repel insects from the cupboard. Alternatively, the thin film may be applied to the skin, to repel insects such as mosquitoes from the skin.

In a typical insect stick of the invention, the ETDABP or ETPA content will range from about 5–60 wt. % of the stick, and preferably ranges from about 10–50 wt. %. The content of anti-insect chemical will typically range from 0.1–30 wt. %. The amount of anti-insect chemical to be used in the insect stick will depend on the potency of the anti-insect chemical, as well as its compatibility with the ETDABP or ETPA. Suitable anti-insect chemicals include synthetic pyrethroid, D-empenthrin and DEET, as well as the other insecticides disclosed previously herein. Other anti-insect chemicals as known in the art may also or alternatively be incorporated into the gel of the invention. These anti-insect active ingredients are "emitted" within the meaning of that term as used herein because they either vaporize from the gel or otherwise migrate to the surface of the gel and then contact the surrounding insect-containing environment.

Optional components may be present in the insect stick. These optional components impart desirable properties to the stick, such as color, aroma, texture, enhanced ease of application to a surface, compatibility between the ETDABP or ETPA and the anti-insect chemical so that higher loadings of anti-insect chemical may be present in the stick, etc. A preferred optional component is a hydrocarbon having about 12 to 30 carbon atoms and mixture thereof. The molecular weight and vapor pressure of the hydrocarbon may be selected with a view to its effect on the release properties of the anti-insect chemical. A more volatile hydrocarbon, e.g., $C_{10}$–$C_{18}$ volatile hydrocarbons, will tend to carry the active ingredient to the surface of the gel, thereby making the active ingredient more available to the environment. A hydrocarbon having a relatively high number of carbon atoms, for example squalene or other skin oil, may also be desirably included within the insect stick if the stick will be used to contact the skin. The skin oil may reduce any irritation that could arise when the skin contacts the anti-insect chemical.

The controlled release composition of the invention may be prepared by combining ETDABP with the active ingredient(s), and heating these with stirring until a uniform mixture results. Upon cooling, the mixture will assume a gel or stick-like consistency. One or more solvents as described above may also be present in the composition.

If an optional hydrocarbon component is to be present in the composition, then a preferred method of preparing the controlled release composition is to heat the hydrocarbon and the ETDABP or ETPA gellant with stirring until a homogeneous mixture results. Typically, this is achieved within a temperature range of about 80–120° C. While higher temperatures may be employed, no benefit arises as a result of such higher temperatures. After the molten homogeneous mixture of hydrocarbon and gellant is formed, the mixture may be cooled before adding the active ingredient(s). This pre-cooling step is particularly preferred when the active ingredient is volatile, and is less important for non-volatile active ingredients. After stirring the active ingredient(s) into the composition, the composition is allowed to cool whereupon a gel forms.

ETDABP in combination with one or more solvents, and optionally containing one or more additional ingredients such as fragrance, may form a transparent, rigid and stable gel. These gels may be used to form flammable objects (e.g., candles and fuels), or objects that emit active ingredients. The gels of the present invention are particularly desirable because they demonstrate each of the properties of transparency, rigidity and stability, which cannot be said of the prior art gels. Before describing the various ways in which ETPA may be formulated to provide desirable gels of the invention, some discussion regarding each of transparency, rigidity and stability in the context of the present invention is provided.

As used herein, the term "rigidity" refers to the amount of deflection which a gel displays when responding to a force. More specifically, rigidity may be measured by holding a cylinder (or similar shape) of gel material in a horizontal direction. The extent to which the cylinder bends toward the earth under the force of gravity is used as a measure of the rigidity of the gel. A very rigid gel will not bend to any noticeable degree, while a gel that exhibits little or no rigidity will display considerable bend.

In order to impart quantitative meaning to the term "rigid", the test described below has been devised, which provides a measure of rigidity in terms of a "deflection value". The deflection values may range from a minimum of zero to a maximum of 90, where completely rigid material does not show any deflection and thus has a deflection value of zero, while a very flexible/limp material will show the maximum deflection and be described by a deflection value of 90.

Figure 5:
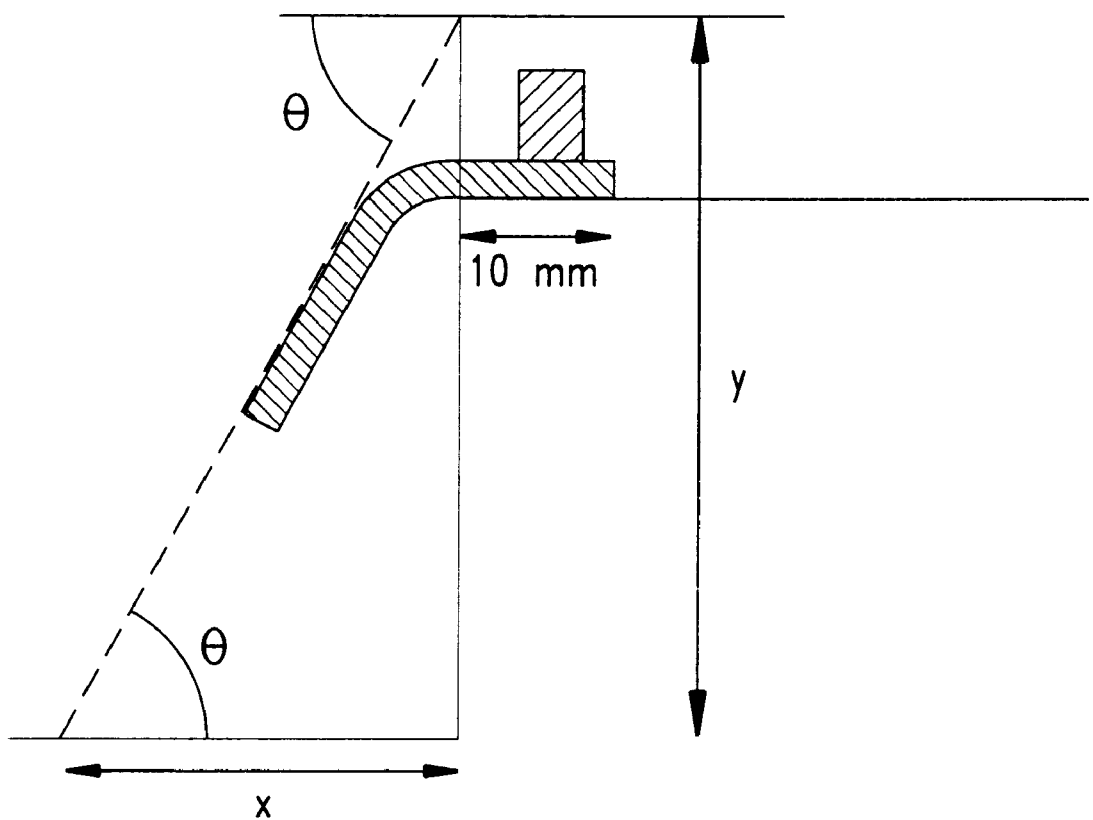
FIG. 5 illustrates a testing protocol for measuring the rigidity of a sample.

The testing protocol is illustrated in FIG. 5. A gel sample having dimensions 57×10×3 mm is placed on a flat horizontal surface, such that 10 mm of the sample is on the surface and the remainder of the sample extends over the side of the surface and is unsupported. The degree to which the unsupported portion of the sample bends downward provides the deflection value. Thus, if the sample does not bend downward at all, it is assigned a deflection value of 0, because the unsupported portion is directed at an angle of 0° different from the supported portion of the sample. However, if the unsupported portion of the sample bends straight downward as soon as it is unsupported, then this sample has a deflection value of 90 because the unsupported and supported portions form a 90° angle with respect to each other. A material with a lower deflection value, which corresponds to a material with higher rigidity, is most desirable for a candle.

Using this test, gels formed from ETPA and hydrocarbon oil may have a deflection value of essentially zero (0), while a gel formed from Kraton® according to the prior art has a deflection value of about 80. If some flexibility (ie., non-rigidity) is desired in an object according to the present invention, it can be achieved by appropriate selection of the gellant and solvent. Thus, the present invention provides gels having deflection values of less than or equal to 70, more preferably less than or equal to 60, still more preferably less than or equal to 50, yet more preferably less than or equal to 40, and still more preferably less than or equal to 30, yet still more preferably less than or equal to 20, further still more preferably less than or equal to 10, and further still more preferably less than or equal to 5, and most preferably equal to or essentially equal to zero. As the deflection value of the gel increases, a candle prepared from such a gel can form a free-standing pillar shape, which will not flop over at the slightest (or even a significant) touch.

Not only may the ETPA gels of the present invention be formulated such that they are rigid, they may also simultaneously be transparent. There are various degrees of transparency, ranging from crystal clear to hazy, which may be achieved with gels of the invention. In order to provide some measure of the absolute transparency of a gel, the following test has been devised. A white light is shined through a gel sample of a given thickness at room temperature, and the diffuse transmittance and the total transmittance of the light are determined. The percent haze for a sample is determined by the equation: % haze=(diffuse transmittance/total transmittance)×100. Samples are prepared by melting the gel (or product made therefrom) and pouring the melt into 50 mm diameter molds. The samples may be prepared at two thicknesses, e.g., 5.5±0.4 mm and 2.3±0.2 mm.

Clarity measurements are made on a Hunter Lab Ultrascan Sphere Spectrocolorimeter using the following settings: specular included, UV off, large area of view, illuminate D65, and observer 10°. Using this protocol with a 2.3 mm thickness sample, an ETPA gel of the present invention may have a % haze value of less than 5, while paraffin wax has a % haze value of over 90. The % haze value for a gel of the present invention can be increased if desired, by appropriate selection of solvent and gellant. Thus, the present invention provides gels (and articles made therefrom) having a transparency (measured by % haze) of less than 75, preferably less than 50, more preferably less than 25, still more preferably less than 10, and yet still more preferably of 5 or less.

The gels of the invention are also stable, in that they preferably do not display syneresis. As defined in the McGraw-Hill Dictionary of Scientific and Technical Terms ($3^{rd}$ Edition), syneresis is the spontaneous separation of a liquid from a gel or colloidal suspension due to contraction of the gel. Typically, syneresis is observed as the separation of liquid from a gel, and is sometimes referred to as "bleeding", in that wetness is seen along the surfaces of a gel that displays syneresis. From a commercial point of view, syneresis is typically an undesirable property, and the gels of the present invention desirably, and surprisingly do not exhibit syneresis.

The gels of the invention, and articles prepared therefrom, may be stable in the sense that they do not exhibit syneresis. Thus, they do not have an oily feeling when handled. Furthermore, they have little or not tendency to flare when lit, due to the presence of a pool or coating of a flammable liquid which has been exuded due to syneresis.

The ETDABP or ETPA gels as described above (as well as additional gels described below) may be encased in whole or part by a solid coating. As used herein, the term encased means "covered by", so that an article at least partially encased by a coating has a coating overlying at least some of the gel. The coating preferably directly contacts the exterior surface(s) of the gel. The coating may be present when the gelled article is primarily intended to be burned, or on a gelled article which is intended primarily to emit an active substance. The coating may confer one or more of a number of possible benefits to the gel.

For instance, any oily feel that may be sensed upon handling the gel is eliminated when a coating is placed on the gel. The coating typically has a non-oily feel, and in fact typically feels dry to the touch. A gel absent the coating will tend to pick up fingerprints when it is handled. The coating does not so readily receive fingerprints, and thus the invention provides that a gel may be repeatedly handled by a consumer without leaving telltale fingerprints, so long as the gel contains a coating as described above.

In addition, the coating typically imparts some mechanical strength to the article, which would not be present in its absence. Gels are often somewhat soft, and may benefit from the increased mechanical strength during, for example, shipping and storage of the article.

The coating may also enhance the clarity of the gelled body by imparting a rigid yet very smooth surface to the body. The coating may be made to be extremely smooth and to have a highly polished appearance. Even when the underlying gel itself is transparent, the surface of the gel may not be completely smooth, in part due to a degree of softness that is typically present in a gel. However, when a hard transparent coating is placed on the surface of a gel, then a very smooth and flawless exterior surface can be achieved. This smooth surface imparts a greater appearance of clarity to the gel. The transparent coating may also improve the refractive index of the exterior of the gel.

When the gel has been formulated primarily for the purpose of emitting an active substance, the coating may be used to effect the rate at which the active component(s) is released and contacts the surrounding environment. For instance, the coating may be used to inhibit the release of the active component, so that a smaller yet still effective amount of active ingredient contacts the environment for a longer period of time. Thus, the coating, besides improving the appearance and feel of a gelled article, can also control the release of volatile fragrance components from a gel. For example, a highly crosslinked thermosetting coating such as an epoxy may be used to slow the release rate of volatile fragrance components from a gelled fragrance release device, which would increase the service life of this article. The characteristics of the coating, such as the chemical functionality and free volume, and the manner in which the coating is applied, including the coating thickness and the area of gel coated, may be varied to control the release rates of various fragrance components from the gelled article.

The coating is preferably clear and colorless or essentially colorless. In addition, the coating is solid, preferably not brittle, and yet not so soft that it is easily deformed after application to the gelled body. The coating may contain optional ingredients, such as fragrance, UV-inhibitors, antioxidants, insect-repellents, and the like.

In a preferred embodiment, the coating includes thermoplastic polymer. A preferred thermoplastic polymer is a polyamide resin formed from dimer acid and diamine, and possibly optional components. The dimer acid-containing (or "based") resins are commercially available from many sources, including Union Camp Corporation, Wayne N.J. under the UNI-REZ trademark, and Henkel Corporation, Ambler, Pa. under the MACROMELT trademark. They are essentially the reaction product of polymerized fatty acid as described above, and diamine. Optional reactants include monoamine, diacid other than polymerized fatty acid, refined trimer acid, monocarboxylic acid, and others known in the art. Because these polyamides have been sold commercially for about 50 years, and are well known in the art, the following description of dimer acid-based polyamides is abbreviated.

Dimer acid-based polyamides are the reaction product of dimer acid as defined above, with diamines. The term "diamine" refers to a molecule having two amine groups, where the amine groups are both preferably primary (e.g., ethylene diamine, hexamethylene diamine, ether diamines, etc.), however may be secondary (e.g., piperazine). The molecular weight of the polyamide will depend, in part, on the relative amounts of dimer acid and diamine used in its formulation. The addition of monofunctional acids (e.g., stearic acid, oleic acid, isostearic acid, etc.) or monofunctional amines may also be used to form low molecular weight polyamides. The dimer acid may be hydrogenated or non-hydrogenated, and co-diacids such as azeleic, sebacic, etc. may be used in the formation of the polyamide In general, a low molecular weight dimer acid-based polyamide is a preferred coating component, and is more preferably the only component of the coating. Such low molecular weight polyamides are preferred because they typically achieve a low viscosity molten state at a relatively lower temperature than may be achieved from high molecular weight polyamides. In addition, the solubility of a dimer acid-based polyamide in an organic solvent typically increases as the molecular weight of the polyamide decreases. However, polyamides tend to become more brittle as their molecular weight decreases, and so a balance between brittleness and melt viscosity/solubility properties is preferably attained. Uni-Rez® 2620 polyamide resin (Union Camp Corporation, Wayne, N.J.) at 20–40% solids in n-propanol is a suitable solution from which to form a coating on a gelled article of the invention. Such a solution may be applied to the gelled body at room temperature or slightly above room temperature, for example 30–40° C.

The thermoplastic need not be a polyamide. Another suitable thermoplastic is a styrene-acrylic resin. Such resins are commercially available and are used in applications such as inks and floor polishes. S. C. Johnson of Racine, Wis., Air Products of Allentown, Pa. and Rohm and Haas of Philadelphia, Pa. are three of the many commercial suppliers of styrene-acrylic resins. Again, a resin with a relatively low molecular weight is preferred, as it allows for a lower viscosity in a low temperature molten state, and generally has higher solubility in organic solvents.

In another preferred embodiment, the coating may include a thermoset. However, the thermoset needs to have a sufficiently long pot life to enable the coating to be applied to the gelled body before the coating cures. The thermosetting system may be a two component system that is cured by mixing two reactive species such as an epoxy cured with a polyamine or polyamide. Alternatively, the thermoset may be a one component system that is cured by water vapor (e.g., a moisture-curable urethane) or electromagnetic radiation (e.g., a UV-curable acrylate or polyamide, etc.), to name two preferred one component thermosets characterized by their curing agent.

Additional polymers from which a suitable coating for the gelled article of the invention may be formed include, without limitation, polyolefins, polydienes, polyamides, polyurethanes, polyimides, polyesters, polyamide-imides, polyester-imides, polyester-amides, polyketones, polyvinyl acetals, polyvinyl ethers, polyureas, acrylics, alkyds, amino resins, cellulosics, elastomers, epoxies, fluoropolymers, ionomers, maleics, natural resins, oleoresinous varnishes, petroleum resins, phenolics, pine derived resins, Shellac, silicones, styrene resins, vegetable and marine oils, vinyl acetate resins, and vinyl chloride resins.

The coating, whether it contains a thermoplastic or thermoset resin or polymer, may additionally contain one or more optional ingredients. A colorant is a preferred optional ingredient. Colorants as described previously for incorporation into a gelled body may equally well be included in the coating composition. A UV-inhibitor is another optional ingredient. Thus, a UV-inhibitor may be added to the coating to that the coating effectively protects the entire gelled body from UV radiation-induced degradation.

While the present invention provides ETDABP gels at least partially encased by a solid coating, the invention also provides for coated gels made from gellants other than ETDABP. Suitable gellants are known in the art, and representative examples as described below. The solvents which are used in these prior art gels may also be used as the solvent for preparing a gel using ETDABP as the gellant. Furthermore, the material which is coated according to the present invention need not even be in the form of a gel, but can be a solid, such as a wax. Suitable waxes include paraffin wax and polyethylene wax.

For instance, a gel may be prepared by combining a polyamide resin (a gellant) with an oil (a solvent) as described in U.S. Pat. No. 3,645,705 to Miller et al. As set forth in Miller, the polyamide resin may be a long chain linear amide resin derived from the reaction of dimerized linoleic acid with di-or polyamines. The polyamide resin typically has a molecular weight (number or weight average) in the range of 6,000 to 9,000 and a softening point in the range of 185° C. to 48° C., and is capable of producing a gel structure in oil when the solubility of the polyamide in the oil is exceeded. The polyamide resin typically constitutes about 7–50% of the total weight of the gel. The oil may be a natural oil, such as castor oil, peanut oil, safflower oil, sunflower oil, corn oil or cod liver oil, having an iodine value in the range of 40 to 135. The oil may be a light, clear mineral oil. The article is readily formed by combining the various constituents at elevated temperature until a homogeneous mass is formed, and then cooling the mass to provide a gelled body.

Up to about 15% by weight of a methyl ester, such as methyl ricinoleate or methyl oleate, may be added to the composition to improve the stiffness and hardness of the article. An 8-, 10- or 12-carbon primary alcohol may be included within the composition that forms the gel, where the alcohol may serve to overcome a greasy or oily surface characteristic that the gel would otherwise have. The percentage of alcohol by weight should not be more than about 30% of the total material, the preferred range being 10–20%. As an article according to this aspect of the present invention has a coating on at least a portion of the surface of the gelled body, and this coating is intended, in part, to provide a pleasing, non-greasy surface to the gel, the incorporation of a primary alcohol in the formulation is not necessary.

Alternatively, the gel may be formed according to Gunderman et al., as set forth in U.S. Pat. No. 3,819,342. Thus, a thermoplastic polyamide resin and a solvent may be combined to form a gel. The polyamide resin is preferably formed by the reaction of an aliphatic polycarboxylic acid with a di- or polyamine. Most preferred are the reaction products of dimerized linoleic acid with di- or polyamines. These resins have an average molecular weight of between 2,000 and 10,000 and are described in great detail in U.S. Pat. Nos. 2,379,413 and 2,450,940.

The solvent of Gunderman et al. is capable of solubilizing the thermoplastic polyamide resin at a temperature below about 100° C., and is selected from the group consisting of unsaturated fatty acids, unsaturated fatty alcohols, saturated fatty alcohols, esters of fatty acids with polyhydric alcohols such as glycerol, and mixtures thereof. Specific suitable solvents include oleyl alcohol, linolenyl alcohol, palmitoleyl alcohol, linoleyl alcohol, mixtures thereof and the like. $C_6$–$C_{14}$ alcohols such as decanol dodecanol, hexanol, heptanol, octanol, nonanol and tetradecyl alcohol, and/or $C_{10}$–$C_{22}$ fatty acids such as ricinoleic, linoleic, oleic, linolenic, erucic, decylenic, dodecylenic and palmitoleic acids may be employed as the solvent. An ester such as caster oil, coconut oil derivatives, propylene glycol monolaurate, propylene glycol stearate, propylene glycol myristate and the like, may be used as well.

The polyamide and solvent of Gunderman et al. are combined in such a ratio that a gel results. For optimal performance, the article should contain from about 5 to 35 parts by weight of the thermoplastic polyamide resin. A preferred composition is one utilizing such a range of resin with an equivalent amount of oleyl alcohol. The article is readily formed by mixing the ingredients at elevated temperature to form a homogeneous composition, and allowing the composition to cool to a gel state.

Alternatively, the gel may be prepared according to U.S. Pat. No. 3,615,289 to Robert Felton. Thus, a gel may be formed by combining a solid polyamide resin, an alkanol amine or alkanol amide, and one or more stearic acid esters or a mixture of stearic acid esters and stearic acid. The composition comprises about 15 to 35 percent by weight polyamide resin, about 20 to 55 percent by weight of alkanol amine or alkanol amide, and about 1 to 50 percent by weight of stearic acid and esters thereof. The gels of Felton are readily formed by heating the components with stirring at a temperature of about 100–115° C. until the mixture is clear, and then allowing the mixture to cool to a gelled state.

The solid polyamide resin of Felton is the soluble condensation product of an aliphatic dicarboxylic acid and a diamine, the carboxyl and amino groups of adjacent monomer units being condensed to an amide linkage in the resin. The resin may also be based on carboxylic and amine compounds having more than two carboxyl and amino groups respectively. The resin is composed primarily of polyamides of molecular weight within the range of from about 2,000 to about 10,000, and are of the type generally set forth in U.S. Pat. No. 2,450,940. The alkanol amide may be prepared by the reaction of a fatty acid ester and an amine, wherein the ester and the amine are in substantially equal proportions. Among such compounds are the 1:1 and 2:1 (Kritchevsky type) diethanolamides of fatty acids, the 1:1 proportion being preferred. The preferred chain length for the fatty acid is about 14 to 24 carbon atoms. Suitable esters of stearic acid include isopropyl isostearate, butyl stearate, hexadecyl stearate, etc.

The gelled articles (candles) of Felton may contain a polyamide resin having at least some free carboxylic acid groups so that the polyamide resin has reactive character. This component may be present in a proportion of from about 5 to 10 percent by weight of the composition, and acts to prevent "sweating" by inhibiting the migration of the oil components. It also provides a smoother, glossier finish to the gelled body. This reactive polyamide may, but need not be present in the articles of the present invention, because the coating on articles of the present invention achieves the desired surface appearance and feel of the article, without reliance on the reactivity of the polyamide.

As a further alternative, the gel may be prepared by the procedures and reactants set forth in U.S. Pat. No. 5,578,089 to Mohamed Elsamaloty. According to Elsamaloty, a gel may be prepared from a hydrocarbon oil (a "solvent" of the present invention) and a blend of diblock and triblock copolymers based on synthetic thermal plastic rubbers. The hydrocarbon oil may be a cosmetic grade hydrocarbon oil (natural or synthetic) and is preferably a white oil. The oil may be a paraffinic oil, a naphthenic oil, natural mineral oil or the like. The rubber blend is prepared from at least one diblock and at least one triblock copolymer, in addition to one or more of radical copolymers and multiblock copolymers. Kraton® rubbers from Shell Chemical Company, which include styrene-butadiene-styrene copolymers and styrene-isoprene-styrene copolymers, are preferred. The gel is formed by blending the polymers and the oil, and then heating the blend to between about 50–90° C. to dissolve the polymers in the oil. Mixing may be carried out in any conventional manner. On cooling, a gel forms.

In one embodiment, the gel preferably consists of about 80–99 wt. % hydrocarbon oil and about 1–20 wt. % of a blend of rubbers, where the rubbers are a blend of at least two different polymer members selected from the group consisting of diblock copolymers, triblock copolymers, radial block copolymers and multiblock copolymers, the gel including at least one diblock copolymer and at least one triblock copolymer, with the diblock and triblock polymers comprising segments of styrene monomer units and rubber monomer units. In another embodiment, the gel comprises from about 70% to about 98% by weight of a hydrocarbon oil, from about 2% to about 30% by weight a copolymer selected from the group consisting of a triblock, radial block and multiblock copolymer, and from 0 to about 10% by weight of a diblock copolymer, as described in, e.g., International Publication No. WO 97/08282.

As disclosed above, there are numerous compositions from which to form a gelled body comprising a gellant and a solvent, where the disclosure above is merely exemplary. Regardless of how the gelled body is formed, and regardless of its composition, in one aspect the present invention provides for an article comprising a gelled body having a solid coating on at least a portion of the surface thereof, where the coating preferably includes at least one of thermoplastic polymer or thermoset polymer. The coating is not of exactly the same composition as the underlying fuel or gel.

The coating can be placed on the gelled body by various techniques. For example, the coating composition may be solid at room temperature but liquid at elevated temperature. In this case, the coating composition may be taken to a molten state and then the gelled body dipped briefly therein, to thereby adhere a layer of coating onto the surface of the body. When the coating composition is soluble in a solvent, then a solution of the coating composition may be prepared and the solution applied to the surface of the gelled body by, e.g., spraying or brushing at, e.g., room temperature. Alternatively, the gelled body may be dipped into the coating composition solution. Normal propanol is a suitable solvent for thermoplastic polymers as discussed above. When the coating composition is applied in the absence of a solvent, it will be referred to as a neat coating composition or a solvent-free coating composition.

When a neat coating composition is applied to the surface of a gelled body, the coating composition should have a melting point that is above room temperature since the coating must be a solid at room temperature. However, the melting point of the coating composition should not be too far above the melting point of the gelled body since dipping the gelled body into a very hot coating composition might melt or otherwise degrade the gelled body. Thus, the identity of the neat coating composition will depend, to some extent, on the identity of the gelled body. In addition, when a neat coating composition is employed to form the article, the viscosity of the molten coating composition should be low enough that the gel can easily be dipped, without significant resistance due to the viscoelasticity of the coating composition.

When a coating composition solution is to be applied to the gelled body, it is preferred that the solvent or solvents be sufficiently volatile that the coating dries in a reasonable amount of time. Also, the choice of solvent(s) will effect the degree to which the coating composition wets the surface of the gelled body, and thus the solvents should be selected with this point in mind. The ability of various solvents to wet various surfaces has been extensively studied and published in the open literature, and thus one of ordinary skill in the art is aware of how to select appropriate solvents depending on the identity of the gelled body. In general, aqueous solvents tend not to wet the gelled body, while short chain alcohols, such as n-propanol and iso-propanol, are quite satisfactory. An aqueous dispersion of a resin may be used as a coating solution, however typically some wetting-enhancement additive, e.g., n-propanol, must be added to provide for good coating of the gelled body by the aqueous coating composition.

The coating thus preferably directly contacts the exterior surface of the underlying gel and at least partially encases that gel. Where the gel has a top, a bottom and one or more sides, the coating preferably covers all of the sides of the gel, and optionally the top and bottom. The coating preferably covers all of the sides of the gel because this is the area of the gel which is primarily seen by the consumer. The coating should conform to the exterior surface of the gel, in that the coating is in direct contact with all of the surface which is covered by the coating. If the gel has a patterned exterior surface, e.g., relief images or a ribbed texture, then the coating either follows the exact contours of the pattern so that the exterior surface of the coating likewise contains that (or perhaps a different) pattern, or that portion of the coating which directly contacts the gel will be conformal in exactly following the contours of the gel's surface but the exterior surface of the coating is smooth and without pattern. Where the exterior surface of the coating is smooth but the exterior surface of the gel has a relief image, the coating should be transparent so that the underlying relief image can be viewed through the coating.

In forming an article comprising a gel having a coating thereon according to the present invention, it is most convenient to first form the gel, and then apply the coating to the surface of the gel. As an alternative, the solid coating may be prepared first, and the molten gel may be poured into the solid coating. For example, the material which forms the solid coating may be applied to the interior surfaces of a mold, and then the molten mixture of gellant and solvent poured into the coating-lined mold. If the solid coating has sufficient structural integrity, it may formed into a desired shape, and the molten mixture of gellant and solvent poured therein.

The gelled bodies of the present invention, with or without coatings thereon, may be used in industrial products such as fuels (sterno, candles, lighters). For example, hydrocarbon gelled with an ETDABP gellant may be used as a heat source in, e.g., a cooking apparatus used in camping and hiking. Such a composition will not flow if tilted, and thus may be safer and neater than similar products made from flowing materials. When the product does not have a coating, then the gellant is preferably an ETDABP, and more preferably is an ETPA gellant.

The flammable articles of the present invention may or may not include a solid coating. In some respects, the presence of a solid coating is desirable because it adds to the mechanical strength of the article, where enhanced mechanical strength is desirable during shipping and storage of the flammable article. In addition, the solid coating essentially eliminates any oily feeling and fingerprinting on the candle, and effectively reduces syneresis because the coating effectively holds in any oils that may tend to leach out of the gelled body due to syneresis. The solid coating may additionally contain one or more of fragrance, insect-repellent, UV-inhibitor and anti-oxidant. Also, the solid coating may contain a pattern, e.g., a relief image, which adds to the aesthetic appeal of the coated article.

The ETDABP gellant may be incorporated into commercial products such as those listed above by blending the ETDABP gellant with the other components of the product. Typically, the ETDABP gellant will be present at a concentration of about 1% to about 50% of the composition, based on the total weight of the composition. It is a routine matter to optimize the amount of ETDABP gellant to have present in a composition, and indeed the amount will vary depending on the actual product and the desired consistency of the product. In general, as more gellant is used in a formulation, the gelled body will display a more pronounced gel character.

The following examples are set forth as a means of illustrating the present invention and are not to be construed as a limitation thereon.

In the following Examples, softening point was measured using a Model FP83HT Dropping Point Cell from Mettler Instruments Corporation, with a heating rate of 1.5° C./min. Viscosity measurements were made using a Model RVTD Digital Viscometer from Brookfield Engineering Laboratories, Inc., and are reported in centipoise (cP). Gel clarity and hardness were both judged qualitatively.

In the synthesis Examples that follow, and unless otherwise noted, the chemicals were all of reagent grade, obtained from commercial supply houses including Aldrich Chemical Co. (Milwaukee, Wis.) and the like. Unidyme® 14 polymerized fatty acid is a dimer acid available from Union Camp Corp., Wayne, N.J. Empol® 1008 polymerized fatty acid is a dimer acid available from Henkel Corporation, Ambler, Pa. Pripol™ 1008 polymerized fatty acid is a dimer acid available from Unichema North America, Chicago, Ill. Harchemex® (Union Camp Co., Wayne N.J.) alcohol is a 60/40 blend of $C_{14}/C_{16}$ linear alcohols. As used herein, "BBA" stands for the company Bush Boake Allen, located in Montvale, N.J.

EXAMPLES

Example 1

ETPA From $C_{14}$–$C_{16}$ Linear Alcohol

This Example shows that a clear, soft gel can be made with an ETPA synthesized from a blend of linear alcohols having chain lengths of 14 and 16 carbons The components and amounts thereof as shown in Table 1 were charged to a reaction vessel and heated at 200–220° C. under a nitrogen atmosphere for 2 hours. The resulting ETPA had a softening point of 68.5° C. and a viscosity of 44 centipoise at 130° C., as summarized in Table 2.

TABLE 1

REACTANTS USED TO FORM A
LINEAR C14/C16 ALCOHOL-TERMINATED POLYAMIDE

| Reactant | % Equivalents | Weight % |
|---|---|---|
| Unidyme ® 14 | 100 | 65.6 |
| Hexamethylene diamine | 50 | 6.5 |
| Harchemex ® | 50 | 27.8 |

This ETPA was combined with tetradecane (20 wt. % ETPA/80 wt. % tetradecane) and heated until the ETPA dissolved in the tetradecane. Upon cooling to room temperature, the solution formed a soft clear gel, summarized in Table 2.

Example 2

ETPA From $C_{22}$ Linear Acohol

This example shows that a clear, soft gel can be made with an ETPA synthesized from a linear alcohol having a chain length of 22 carbons.

The starting materials used to prepare the ETPA are identified in Table 3 and the properties of the resulting ETPA are given in Table 2. The gellant and the gel were made in the manner described in Example 1.

TABLE 3

REACTANTS USED TO FORM A
LINEAR $C_{22}$ ALCOHOL-TERMINATED POLYAMIDE

| Reactants | % Equivalents | Weight % |
|---|---|---|
| Pripol ™ 1009 | 100 | 56.6 |
| Hexamethylene diamine | 40 | 4.6 |
| Behenyl alcohol | 60 | 38.8 |

Example 3

ETPA From $C_{18}$ Linear alcohol

This example shows that a clear, soft gel can be made with an ETPA synthesized from a linear alcohol having a chain length of 18 carbons.

Using the reactants identified in Table 4, an ETPA was synthesized by charging the diacid and alcohol to a reaction vessel at room temperature, heating the mixture under nitrogen to 80° C., adding the diamine, heating to 220° C., holding at 220° C. for 1 hour, and finally holding under vacuum (8–10 mbar) at 220° C. for 2 hours. As summarized in Table 2, the ETPA had a softening point of 85.7° C. and a viscosity at 190° C. of 27 cP.

TABLE 4

REACTANTS USED TO FORM A
LINEAR $C_{18}$ ALCOHOL-TERMINATED POLYAMIDE

| Reactant | % Equivalents | Weight % |
|---|---|---|
| Empol ® 1008 | 100 | 71.9 |
| Ethylene Diamine | 65 | 4.8 |
| Stearyl Alcohol | 35 | 23.3 |

A gel was formed from this ETPA according to the procedure described in Example 1. As characterized in Table 2, the gel was clear and hard.

A second gel was formed from this ETPA by combining 60 weight percent ETPA with 40 weight percent mineral oil, heating the mixture to homogeneity, and then cooling to room temperature to form a gelled body. The gelled body was clear, however somewhat soft, with a melting point of 95° C. A wick was placed in the gelled body to form a candle. Upon burning, the candle had a flame height of 0.5 inches, a pool size of 1.5 inches (pool size is the diameter of the pool of molten candle that is present at the point where the wick enters the gelled body), and exhibited some coking and the burned area exhibited slight discoloration.

A third gel was formed from 45 parts ETPA, 50 parts mineral oil (Drakeol® 7 from Penreco) and 5 parts fragrance (product number 564-24392 from Bush Boake Allen of Montvale, N.J.). This gel was colored with 0.001% Pylakrome Red (Pylam Products, Tempe Ariz.) in mineral oil, to provide a crystal clear candle with excellent consistency.

A fourth gel was formed from 45 parts ETPA, 49.7 parts mineral oil, 5 parts fragrance (product number 564-24392 from Bush Boake Allen of Montvale, N.J.) and 0.3 parts Lumi Nova® G300C (United Mineral & Clay Corp., Lyndhurst, N.J.). A wick was then added. The results was a slightly translucent candle which, after being placed in the sun for 1 hour, emitted a glow in a darkened space for at least 1 hour. The candle had excellent consistency, being sufficiently firm to hold itself up in a tapered candle form.

Example 4

ETPA From $C_{24}$ Branched-Chain Alcohol

This example shows that a clear, hard gel can be made with an ETPA synthesized from a branched alcohol having a chain size of 24 carbons.

An ETPA was synthesized according to the procedure described in Example 3, using the reactants as identified in Table 5. The resultant ETPA gellant had a softening point of 85.2° C. and a viscosity of 20 cP at 190° C.

TABLE 5

REACTANTS TO FORM A BRANCHED $C_{24}$ ALCOHOL-TERMINATED POLYAMIDE

| Reactant | % Equivalents | Weight % |
|---|---|---|
| Empol ® 1008 | 100 | 64.7 |
| Ethylene Diamine | 60 | 4.0 |
| Iso Tetracosanol | 40 | 31.3 |

A gel was prepared from this ETPA according to the procedure described in Example 1. As summarized in Table 2, the gel was clear and hard.

Example 5

ETPA From $C_{10}$ Linear Alcohol

This example shows that an opaque gel in tetradecane is formed when an ETPA made from a linear alcohol having a chain length of 10 carbons is used.

The ETPA was synthesized in the manner described in Example 3 using the reactants identified in Table 6. As summarized in Table 2, the ETPA had a softening point of 93.2° C. and a viscosity at 190° C. of 29 cP.

TABLE 6

REACTANTS TO FORM A LINEAR $C_{10}$ ALCOHOL-TERMINATED POLYAMIDE

| Reactant | % Equivalents | Weight % |
|---|---|---|
| Empol ® 1008 | 100 | 79.5 |
| Ethylene Diamine | 65 | 5.4 |
| n-Decanol | 35 | 15.1 |

This ETPA was combined with tetradecane to form a gel according to the procedure of Example 1. The gel was opaque and hard, as summarized in Table 2.

Example 6

ETPA With Moderate $C_4$ Linear Alcohol Termination

This example shows that an opaque gel in tetradecane is formed when an ETPA made from a linear alcohol having a chain length of 4 carbons is used.

With one exception, the ETPA was synthesized in the manner described in Example 3, using the reactants set forth in Table 7. In this Example however, excess butanol was added to the formulation before the vacuum stage, to thereby reduce the acid number to 10–15. As summarized in Table 2, the gel had a softening point of 86.3° C. and a viscosity of 35 cP at 190° C.

TABLE 7

REACTANTS USED TO FORM A LINEAR $C_4$ ALCOHOL-TERMINATED POLYAMIDE

| Reactant | % Equivalents | Weight % |
|---|---|---|
| Empol ® 1008 | 100 | 86.5 |
| Ethylene Diamine | 65 | 5.8 |
| n-Butanol | 35 | 7.7 |

A gel was made from this ETPA as described in Example 1. The gel was opaque and soft, and showed syneresis (i.e., "bleeding" of tetradecane from the gel), which is undesirable.

Example 7

ETPA From With High $C_4$ Linear Alcohol Termination

This example shows that a clear gel in tetradecane is formed when an ETPA made from a linear alcohol having a chain length of 4 carbons at a relatively high concentration (50% eq.) is used.

An ETPA was synthesized in the manner described in Example 6, again using excess butanol before the vacuum stage in order to reduce the acid number to 10–15. The reactants used to form this ETPA are set forth in Table 8. The product ETPA has a softening point of 77.2° C. and a viscosity of 15 cP at 190° C.

TABLE 8

REACTANTS USED TO FORM A LINEAR $C_4$ ALCOHOL-TERMINATED POLYAMIDE

| Reactant | % Equivalents | Weight % |
|---|---|---|
| Empol ® 1008 | 100 | 84.8 |
| Ethylene Diamine | 50 | 4.4 |
| n-Butanol | 50 | 10.8 |

A gel was made using this ETPA, according to the procedure described in Example 1. The gel was clear and hard (see Table 2).

Example 8

ETPA With Low $C_{18}$ Linear Alcohol Termination

This example shows that there is a lower limit to the alcohol concentration that can be used in an ETPA, and still obtain a transparent gel therefrom. Below this limit, opaque gels in tetradecane are formed.

An ETPA was synthesized according to the procedure of Example 3, using the reactants identified in Table 9. The ETPA has a softening point of 90.4° C. and a viscosity of 47 cP at 190° C.

TABLE 9

REACTANTS USED TO FORM A LINEAR $C_{18}$ ALCOHOL-TERMINATED POLYAMIDE

| Reactant | % Equivalents | Weight % |
|---|---|---|
| Empol ® 1008 | 100 | 76.4 |
| Ethylene Diamine | 75 | 5.9 |
| Stearyl alcohol | 25 | 17.7 |

This ETPA was formed into a gel according to the procedure outlined in Example 1. The gel was hard but opaque, as summarized in Table 2.

A second gel was prepared by combining 40 parts of this ETPA with 60 parts of mineral oil. These two ingredients were heated until homogeneous, and then allowed to cool. During the cooling process, a wick was added to the gelled body, in order to form a candle. The gelled body was clear and hard, with a melting point of 110° C. Upon burning, the flame height was 0.5 inches, and the pool size (as defined in Example 3) was 1.25 inches. There was a little coking, but less than the amount observed with the candle of Example 3. There was no discoloration in the burned area.

Example 9

ETPA From With Very High $C_{24}$ Branched-Chain Alcohol Termination

This example shows that a there is an upper limit to the alcohol concentration that can be used in a forming an ETPA, and still obtain a hard gel. Above this limit, clear, extremely soft gels in tetradecane are formed.

An ETPA was synthesized as in Example 1, using the reactants set forth in Table 10. The ETPA was very soft, having a melting point below room temperature. The viscosity of the ETPA at 130° C. was 20.5 cP.

TABLE 10

REACTANTS USED TO FORM A BRANCHED $C_{24}$ ALCOHOL-TERMINATED POLYAMIDE

| Reactant | % Equivalents | Weight % |
|---|---|---|
| Empol ® 1008 | 100 | 51.5 |
| Hexamethylene Diamine | 30 | 3.1 |
| Iso Tetracosanol | 70 | 45.4 |

A gel was prepared from this ETPA as described in Example 1. The gel was clear but very soft, as summarized in Table 2.

Example 10

ETPA From Co-Diacid and $C_{18}$ Linear Alcohol

This example shows that a co-diacid can be added to the ETPA formulation to increase the gel hardness while maintaining clarity.

An ETPA was synthesized as in Example 3, charging the co-diacid before heating. The reactants listed in Table 11 were used to form this ETPA. The product had a softening point of 133.5° C. and a viscosity at 190° C. of 26 cP.

TABLE 11

REACTANTS USED TO FORM A LINEAR $C_{18}$ ALCOHOL-TERMINATED POLYAMIDE WITH 10% SEBACIC ACID

| Reactant | % Equivalents | Weight % |
|---|---|---|
| Empol ® 1008 | 90 | 67.8 |
| Sebacic Acid | 10 | 2.7 |
| Ethylene Diamine | 65 | 5.1 |
| Stearyl alcohol | 35 | 24.4 |

Using the procedure of Example 1, a gel was formed from this ETPA. The gel was clear and hard, as summarized in Table 2.

TABLE 2

THE PHYSICAL AND GEL PROPERTIES OF ETPAs MADE FROM VARIOUS ALCOHOL SIZES AND CONCENTRATIONS

| Ex. No. | Alcohol Chain | Alc. Conc. (% eq.) | Soft. Pt. (° C.) | Viscosity (cP) | 20 wt. % ETPA in tetradecane |
|---|---|---|---|---|---|
| 7 | 4 (linear) | 50 | 77.2 | 15 @ 190° C. | clear, hard gel |
| 6 | 4 (linear) | 35 | 86.3 | 35 @ 190° C. | opaque, soft gel, syneresis |
| 5 | 10 (linear) | 35 | 93.2 | 29 @ 190° C. | opaque, hard gel |
| 1 | 14, 16 (linear) | 50 | 68.5 | 44 @ 130° C. | clear, soft gel |
| 3 | 18 (linear) | 35 | 85.7 | 27 @ 190° C. | clear, hard gel |
| 8 | 18 (linear) | 25 | 90.4 | 47 @ 190° C. | opaque, hard gel |
| 10 | 18 (+10% sebacic) | 35 | 133.5 | 26 @ 190° C. | clear, hard gel |
| 2 | 22 (linear) | 60 | 73.1 | 36.5 @ 130° C. | clear, soft gel |
| 9 | 24 (branched) | 70 | ≈RT | 20.5 @ 130° C. | clear, very soft gel |
| 4 | 24 (branched) | 40 | 85.2 | 20 @ 190° C. | clear, hard gel |

Example 11

Effect of Alcohol Chain Length on Gel Clarity

This Example shows that the chain length of the alcohol used to prepare an ester-terminated polyamide, will have an affect on the clarity of the gel made from that polyamide. This Example further shows that the concentration of gellant in a hydrocarbon medium will affect the clarity of the gel.

The ester-terminated polyamides of Example Nos. 6 ($C_4$ linear alcohol), 5 ($C_{10}$ linear alcohol) and 3 ($C_{18}$ linear alcohol) were dissolved in hot tetradecane at concentrations ranging from 10 to 30 wt. % based on the total weight of ETPA and tetradecane. Upon cooling, the resulting gels were evaluated for clarity with the results as set forth in Table 12.

TABLE 12

GEL CLARITY AS A FUNCTION OF GELLANT CONCENTRATION AND THE CHAIN LENGTH OF THE ALCOHOL USED TO PREPARE THE GELLANT

| Example Number | Alcohol Chain Length | Wt. % Gellant In Tetradecane + Gellant Mixture | | | |
|---|---|---|---|---|---|
| | | 10 | 15 | 20 | 30 |
| 6 | $C_4$ | Opaque | Opaque | Opaque | Opaque |
| 5 | $C_{10}$ | Opaque | Opaque | Opaque | Translucent |
| 3 | $C_{18}$ | Opaque | Clear | Clear | Clear |

The data of Table 12 shows that none of the ETPAs form clear gels at 10 wt. % solids. At 15 wt. % and 20 wt. % gellant using tetradecane, only the stearyl alcohol-terminated polyamide forms clear gels.

Example 12

Effect of Hydrocarbon on Gel Hardness and Clarity

When the ETPAs of Example 11 were used to form gels in decalin, the gels showed improved clarity however tended to be softer. The clarity behavior described in Example 11 is essentially reproduced when tetradecane is replaced with isooctane or with PD 23 (a hydrocarbon blend from Witco, Corp., Greenwich, Conn.). In isooctane, a gel tends to be harder compared to when decalin is used, however softer than when tetradecane is used.

Example 13

ETPA Composition Used For Gelling a Hydrocarbon Solvent

This example shows how an ETPA can be used to produce a clear, hard gel in PD 23 hydrocarbon, where PD 23 is a petroleum distillate made by Witco (Greenwich, Conn.) that has a viscosity of 2.6 cSt at 40° C. and a flash point of 230° F. PD-23 hydrocarbon is used in household products such as furniture polishes, household cleaners, liquid candles, and hand cleaners.

A gel was prepared from the ETPA made according to Example 3. The gel was made by heating 20% (by weight) of the ETPA in PD-23 until the ETPA had dissolved. The solution was allowed to cool and a clear, hard gel was formed.

Example 14

ETPA Gel With KLEAROL Hydrocarbon

This example shows how the ETPA prepared as in Example 3 can be used to gel a low viscosity, white mineral oil. The mineral oil used was Klearol® (Witco Corp., Greenwich, Conn.) which has a viscosity of 7–10 cSt at 40° C. and a flash point of 310° F. Klearol® mineral oil is used in personal care products such as cleansing creams, hand cleansers, costume makeup, lipsticks, and hair care products. When gelled with the ETPA at 20% solids, the gel was clear and hard.

Example 15

ETPA Gel With KAYDOL Hydrocarbon

This example shows how the ETPA prepared as in Example 3 can be used to gel a high viscosity, white mineral oil. The mineral oil used was Kaydol®, which has a viscosity of 64–70 cSt at 40° C., a flash point of 430° F. and is available from Witco Corp. Kaydol® mineral oil is used in bath oil, suntan oil, moisturizing creams, and foundation makeup. When gelled with the ETPA at 30% solids, the gel was clear and hard.

Example 16

ETPA Gel With a Monofunctional Ester Solvent

This example shows how the ETPA prepared as in Example 3 can be used to gel a mono-functional ester. The ester was a $C_{12-15}$ alkyl benzoate called Finsoly® TN, made by Fintex (Elmwood Park, N.J.). When gelled with the ETPA at 10% solids, the gel was clear and hard.

Example 17

ETPA Gel with a Monofunctional Ester Solvent

This example shows how the ETPA prepared as in Example 3 can be used to gel a mono-functional ester. The ester was isopropyl isostearate (unimate IPIS, made by Union Camp, Wayne, N.J.). When gelled with the ETPA at 20% solids, the gel was clear and hard.

Example 18

ETPA Gel With a Multifunctional Ester Solvent

This example shows that a multi-functional ester can be gelled with the ETPA prepared as in Example 3. The ester was castor oil. When combined with the ETPA at 20% solids, a clear, hard gel was formed.

Example 19

ETPA Gel With Terpene Hydrocarbon Solvent

This example shows that a terpene hydrocarbon solvent can be gelled with an ETPA. An ETPA was prepared using the procedure of Example 8. The resultant ETPA was combined with limonene at 20% solids to yield a clear, firm gel.

Example 20

Comparative Example

In this comparative example, an ETPA was made by first synthesizing a polyamide from Empol 1008 hydrogenated dimer (Henkel Corp. Ambler, Pa.) and EDA resulting in a polyamide with an amine number of 3 and a softening point of 115° C. 100 g of this polyamide was heated under nitrogen with 66 g of Empol 1008 at 230° C. for 50 minutes. The mixture was cooled to 110° C. and 30 g of ethanol and 2 ml of HCl were added. The mixture was heated under reflux conditions and the temperature was allowed to reach 230° C. The acid number was checked periodically and ethanol was added (at 110° C.) until the acid number was less than 30. At 230° C., vacuum was held on the mixture for 0.5 h and the ETPA was poured. The resultant ETPA had an acid number of 25 and a softening point of 80° C.

The ETPA was combined with tetradecane at 20% and heated until the ETPA dissolved. Upon cooling, an opaque, soft gel formed that showed syneresis.

Example 21

Comparative Example

This comparative example repeats Example 20, however the esterification was done at much lower temperatures. The polyamide described in Example 20 (softening point=115° C.) was heated under reflux with Empol 1008 at 230° C. in the same proportions as in Example 20 for 50 min. This mixture was then cooled to 25° C. and ethanol and HCl were added in the same proportions as in Example 20. The mixture was heated under reflux at 80–85° C. for eight hours and the excess ethanol was removed in a nitrogen stream at 100° C. The resultant product had an acid number of 17 and a softening point of 83° C. This material at 20% level was then heated in tetradecane until dissolved. After the mixture cooled, an opaque, soft gel formed that showed syneresis.

Example 22

Comparative Example

This comparative example shows that the ETPA made in Example 21 is capable of thickening linseed oil, a component of alkyd paints. The ETPA made in Example 21 at 10% level was heated in linseed oil until dissolved. Upon cooling, an opaque, thickened product was formed.

Example 23

This example shows that the ETPA made according to the present method thickens linseed oil. The ETPA made in Example 3 at 10% level was heated in linseed oil until dissolved. Upon cooling, an opaque, thickened product was formed.

Example 24

This example shows that an ETPA can be used to gel an oil-based mixture with an active ingredient. 10 g of the ETPA prepared as in Example 8 was heated in 15 g methyl salicylate, 4 g menthol (active ingredient), and 21 g of KAYDOL (white mineral oil) until the ETPA was dissolved. When the solution cooled, a clear, firm gel was formed.

Example 25

Candle Preparation

This Example demonstrates that an ETPA gellant can be used to make a clear candle. The candle was prepared by combining 60 parts Drakeol® 7 mineral oil (from Penreco, a division of Pennzoil Products Company, Karns City, Pa.) and 40 parts of the ETPA prepared in Example 8, and heating the combination to about 110° C. until a clear, visually homogeneous solution is obtained. The hot mixture was then poured into a shallow dish that contains a wick. Upon cooling, a clear, freestanding candle was formed. The candle did not emit smoke when lit, and no discoloration was observed after burning.

Throughout the present specification, where gellants or reaction mixtures are described as including or comprising specific components or materials, it is contemplated by the inventors that the gellants or reaction mixtures may alternatively consist essentially of, or consist of, the recited components or materials. Accordingly, throughout the present disclosure any described composition (gellant or reaction mixture) of the present invention can consist essentially of, or consist of, the recited components or materials.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

Example 26

Preparation of Clear Pillar Candle

An ETPA having the composition and properties as shown in Table 13 was prepared according to the procedure of Example 1.

TABLE 13

COMPOSITION AND PROPERTIES OF ETPA

| ETPA Parameter | |
|---|---|
| Composition (wt. %) | 76% dimer acid (Empol ™ 1008), 6% Ethylene diamine, 18% stearyl alcohol (Alfol ™ 18) |
| color, Gardener | 1–3 |
| softening point (° C.) | 93–98 |
| visc. @ 160° C. (cPs) | 110–160 |
| acid/amine numbers | 14–10/<1 |

This ETPA (of Table 13) was used to prepare a candle having the composition indicated in Table 14 below. The candle was prepared by combining the indicated ingredients (except fragrance) and heating them at 100–110° C. in a beaker with stirring. After the ETPA dissolved, the solution was cooled to 80° C. and the fragrance was added. The solution was then poured into a two-piece plastic mold containing a wick. After cooling, the mold was removed to provide a clear, free standing candle.

TABLE 14

COMPOSITION OF ETPA-BASED CANDLE

| Ingredient | wt. % | Supplier |
|---|---|---|
| ETPA | 40.00 | Union Camp (Wayne, NJ) |
| Mineral Oil (Drakeol ® 7) | 54.85 | Penreco (Houston, TX) |
| Pylakrome ™ Red (1% in mineral oil) | 0.10 | Pylam Products (Tempe, AZ) |
| D&C Violet #2 (0.1% in mineral oil) | 0.05 | Pylam Products (Tempe, AZ) |
| Fragrance | 5.00 | BBA (Montvale, NJ) |

The candle of Table 14 was evaluated and found to have the characteristics set forth in Table 15 below.

TABLE 15

BURNING PROPERTIES OF ETPA-BASED CANDLE

| Property | |
|---|---|
| color (light yellow 1–10 dark yellow) | 2–3 |
| clarity (clear 1–10 opaque) | 2–3 |
| smoking (when lit/during burning/after burning | none |
| intensity of flame (initial/1 h/2 h/4 h/6 h) | bright |
| color of flame (initial/1 h/2 h/4 h/6 h) | bright yellow |

TABLE 15-continued

BURNING PROPERTIES OF ETPA-BASED CANDLE

| Property | |
|---|---|
| height of flame (initial/1 h/2 h/4 h/6 h) | 1 in. |
| size of pool, diameter (1 h/2 h/4 h/6 h) | 1.25/1.25/1.25/1.5 in. |
| color of pool (1 h/2 h/4 h/6 h) | good/good/slight yellow/ slight yellow |
| weight loss (1 h/2 h/4 h/6 h) | 3/7/13/20% |

Example 27

Comparative Examples of Candle Preparation

Two examples of existing candle technology were compared with the ETPA-based clear candle. Table 16 lists the properties and characteristics of a ETPA-based candle versus a Geahlene™ (Penreco, Houston, Tex.) based candle and a paraffin based candle. Geahlene® contains Kraton® rubber. The ETPA candle is free standing and clear. In contrast, the Geahlene® based candle is clear but not free standing, and the paraffin based candle is free standing however opaque (not clear). In addition, the burning characteristics of the ETPA candle are better than the Geahlene™ candle with respect to smoking and flame height, and are better than the paraffin candle with respect to weight loss (longevity).

TABLE 16

COMPARISON OF ETPA CANDLE VERSUS GEAHLENE AND PARAFFIN CANDLES

| Property | ETPA | Geahlene ™ | Paraffin |
|---|---|---|---|
| clarity | clear | clear | opaque |
| free standing | yes | no | yes |
| smoking (when lit/burn/after burn | none | none | some |
| intensity of flame (initial/1h/6H) | bright | low | very bright |
| height of flame (initial/1h/6h) | 1 in. | 0.25 in. | 1.5 in. |
| color of pool (1h/6h) | good/light tan | good/slight yellow | good |
| weight loss (1h/2h/4h/6h) | 3/7/13/20% | 2/4/8/13% | 7/14/30/43% |

Example 28

Preparation of Clear Non-Pillar Candle

A candle was prepared with the ETPA of Example 26 (Table 13), using the procedure also set forth in Example 26 except the hot ETPA/oil solution was poured into a glass jar containing a wick. The candle had the composition set forth in Table 17.

TABLE 17

CLEAR NON-PILLAR CANDLE COMPOSITION

| Ingredient | wt. % | Supplier |
|---|---|---|
| ETPA (see Table 1) | 30.00 | Union Camp (Wayne, NJ) |
| Mineral Oil (Drakeol ® 7) | 64.85 | Penreco (Houston, TX) |
| Pylakrome ™ Red (1% in mineral oil) | 0.10 | Pylam Products (Tempe, Az) |
| D&C Violet #2 (0.1% in mineral oil) | 0.05 | Pylam Products (Tempe, Az) |
| Fragrance | 5.00 | BBA (Montvale, NJ) |

Example 29

Clear Pillar Candle With Insect Repellent

A clear, pillar candle having insect repellent (citronella) was prepared using the ETPA of Example 26 (Table 13), and having the composition shown in Table 18. This candle was prepared according to the procedure of Example 26.

TABLE 18

COMPOSITION OF CLEAR PILLAR CANDLE WITH INSECT REPELLENT

| Ingredient | wt. % | Supplier |
|---|---|---|
| ETPA (see Table 13) | 40.00 | Union Camp (Wayne, NJ) |
| Mineral Oil (Drakeol ® 7) | 46.00 | Penreco (Houston, TX) |
| Citronella Oil | 10.00 | BBA (Montvale, NJ) |
| Fragrance | 4.00 | BBA (Montvale, NJ) |

Example 30

Clear Non-Pillar Candle With Insect Repellent

A clear, non-pillar candle having insect repellent (citronella) was prepared using the ETPA of Example 26 (Table 13), and having the composition shown in Table 19. This candle was prepared according to the procedure of Example 26.

TABLE 19

COMPOSITION OF CLEAR NON-PILLAR CANDLE WITH INSECT REPELLENT

| Ingredient | wt. % | Supplier |
|---|---|---|
| ETPA (see Table 13) | 30.00 | Union Camp (Wayne, NJ) |
| Mineral Oil (Drakeol ® 7) | 63.00 | Penreco (Houston, TX) |
| Citronella Oil | 5.00 | BBA (Montvale, NJ) |
| Fragrance | 2.00 | BBA (Montvale, NJ) |

Example 31

Clear Gelled Body

A clear, gelled body was prepared using the ETPA of Example 26 (Table 13), and having the composition shown in Table 20. This gelled body was prepared according to the procedure of Example 26.

TABLE 20

COMPOSITION OF CLEAR GELLED BODY

| Ingredient | wt. % | Supplier |
|---|---|---|
| ETPA (see Table 13) | 2.00 | Union Camp (Wayne, NJ) |
| Mineral Oil (Isopar ™ K) | 96.00 | Exxon (Houston, TX) |
| Fragrance | 2.00 | BBA (Montvale, NJ) |

Example 32

Effect of Candle Composition on Clarity and Smoking

Candles were prepared as described in Example 28, using the ETPA composition as given in Table 13. The candle composition was 15 wt. % ETPA, 65 wt. % Drakeol® 7, 10 wt. % fragrance 564-27587 (Bush Boake Allen, Montvale, N.J.) and 10 wt. % of a performance additive as set forth below in Table 21.

Table 21 shows the results of analyzing candles having various performance additives, as set forth in the Table. The candles were evaluated on the basis of clarity and smoking, where smoking was characterized on a scale of 1 to 10, where "1" denotes no smoking and "10" denotes heavy smoking.

TABLE 21

ADDITIVE EFFECT ON SMOKING AND CLARITY

| Performance Additive | Clarity | Smoking |
|---|---|---|
| Stearic acid | opaque | 2 |
| Stearyl alcohol | opaque | 2 |
| Myristic acid | clear | 2 |
| Myristyl alcohol | clear | 8 |
| Softigen ® (Huls) $C_{10}$–$C_{18}$ triglyceride | hazy | 10 |
| Neobee ® M5 (Stepan) capric/caprylic triglyceride | hazy | 4 |
| Drakeol ® 7 | opaque | 10 |

The data show that myristyl alcohol improves clarity, however has little effect (compared to Drakeol® 7) on smoking. The data also show that stearic acid and some triglycerides improve smoking performance, but provide little improvement in clarity (again compared to Drakeol® 7). Myristic acid is shown to improve both smoking performance and clarity, versus Drakeol® 7.

Example 33

Clear Candle Displaying Mineral Smoking

Candles were prepared as described in Example 28, using the ETPA composition as given in Table 13. The candle composition was 15 wt. % ETPA, 60 wt. % Drakeol® 7, 10 wt. % fragrance 564-27587 (Bush Boake Allen, Montvale, N.J.) and 5 wt. % of myristic acid. The candle was clear and displayed little or no smoking.

Example 34

Effect of Wick Size on Smoking

Candles were prepared as described in Example 28, using the ETPA composition as given in Table 13. The candle composition was 15 wt. % ETPA, 70 wt. % Drakeol® 7, 10 wt. % fragrance 564-27587 (Bush Boake Allen, Montvale, N.J.) and 5 wt. % myristic acid.

Table 22 shows the data obtained when candles were prepared above, using variously sized wick. As shown in Table 22, a larger wick is preferred in order to minimize the smoking of the candle.

TABLE 22

EFFECT OF WICK SIZE ON SMOKING PERFORMANCES

| Wick Size | Smoking Performance |
|---|---|
| Small wick (<24 ply) | smokes |
| 24 ply | smokes |
| 30 ply | very little smoke |
| Large wick (>30 ply) | no smoke |

Example 35

Fragrance Compatibility With Mineral Oil

Over 150 blends of various fragrance raw materials and mineral oil were prepared at 5% and 10% concentrations. The blends had the characteristics shown in Table 23, where 1=clear, 2=slightly hazy, 3=cloudy, and 4=insoluble.

Gels were then prepared from each of the fragrance materials shown in Table 23, where the gels contained 45 wt. % ETPA (of Table 13), 50 wt. % Drakeol® 7 mineral oil, and 5 wt. % of the fragrance. The vast majority of the gels were clear and did not show syneresis. However, with those fragrance raw materials listed in Table 23 that have a double asterisk "**" next to the name of the material, either some cloudiness was observed in the gel, and/or the gel displayed syneresis.

TABLE 23

FRAGRANCE COMPATIBILITY WITH MINERAL OIL

| Material Code* | Material Name* | 5% | 10% |
|---|---|---|---|
| 160003A | Abbalide IPM | 1 | 1 |
| 100320A | Adoxal NP | 1 | 1 |
| 100440A | Alcohol C-08 | 1 | 1 |
| 100480A | Alcohol C-10 | 1 | 1 |
| 100500A | Alcohol C-11 Undecylic | 1 | 1 |
| 100580A | Aldehyde C-08 | 1 | 1 |
| 100620A | Aldehyde C-10 | 1 | 1 |
| 100640A | Aldehyde C-11 Undecylenic | 1 | 1 |
| 100680A | Aldehyde C-12 Lauric | 1 | 1 |
| 100700A | Aldehyde C-12 MNA | 1 | 1 |
| 100840A | Allyl Amyl Olycolate | 1 | 1 |
| 100860A | Allyl Caproate | 1 | 1 |
| 100900A | Allyl Cyclo Hexyl Propionate | 1 | 1 |
| 100920A | Allyl Heptanoate | 1 | 1 |
| 100960A | Allyl Ionone Extra | 1 | 1 |
| 100060A | Allyl Phenoxy Acetate | 1 | 4 |
| 101064A | Amber Core | 1 | 1 |
| 101300A | Amyl Acetate Primary | 1 | 1 |
| 101578A | Amyl Salicylate | 1 | 1 |
| 101920A | Anisaldehyde** | 3 | 4 |
| 101960A | Anisyl Acetate | 1–2 | 3 |
| 102045A | Anther | 1 | 1 |
| 110015A | Bacdanol | 1 | 1 |
| 110480A | Benzyl Acetate** | 1 | 1 |
| 110515A | Benzyl Alcohol** | 3 | 4 |
| 110550A | Benzyl Benzoate | 1 | 1 |
| 110600A | Benzyl Iso Butyrate | 1 | 1 |
| 110720A | Benzyl Propionate | 1 | 1 |
| 110738A | Benzyl Salicylate | 1 | 1 |
| 111111A | Boisvelone | 1 | 1 |
| 111555A | Butyl Butyrate | 1 | 1 |
| 111615A | Butyl Cinnamic Aldehyde | 1 | 1 |
| 111785A | Butyl Iso Valerate** | 2 | 3 |
| 120410A | Carbitol | 3 | 4 |
| 120060A | Camphor Powder 10%/20% IPM | 1 | 1 |
| 120815A | Cedarleaf Oil American | 2 | 3 |
| 120920A | Cedrenol | 1 | 1 |
| 120960A | Cedryl Acetate Liquid | 1 | 1 |
| 121700A | Cinnamic Alcohol | 3 | 4 |
| 121740A | Cinnamic Aldehyde | 4 | 4 |
| 121900A | Cinnamyl Acetate | 2 | 2 |
| 122018A | Cistulate | 1 | 1 |
| 122060A | Citral CP | 2 | 3 |
| 122100A | Citralva | 1 | 1 |
| 122320A | Citronellene Lactone | 1 | 1 |
| 122356A | Citronellol 750 | 1 | 1 |
| 122410A | Citronellyl Acetate A | 1 | 1 |
| 123320A | Coumarin 10% BB | 1 | 1 |
| 123440A | Cresyl Methyl Ether, Para | 1 | 1 |
| 123680A | Cyclamen Aldehyde | 1 | 1 |
| 123725A | Cyclocitrenellene Acetate | 1 | 1 |
| 123754A | Cyclohexyl Salicylate | 1 | 1 |
| 130007A | Damascone Alpha | 1 | 1 |
| 130280A | Diethyl Malonate | 4 | 4 |
| 130405A | Dihydro Eugenol | 1 | 1 |
| 130420A | Dihydro Myrcenol | 1 | 1 |
| 130428A | Dihydro Myrcenyl Acetate | 1 | 1 |
| 130418A | Dihydrolinalool | 1 | 1 |
| 130435A | Dihydroterpineol | 1 | 1 |
| 130560A | Dimethyl Benzyl Carbinyl Acetate | 1 | 1 |
| 130580A | Dimethyl Benzyl Carbinyl Butyrate | 2 | 3 |
| 130700A | Dimethyl Sulfide** | 1 | 1 |
| 130720A | Dimetol | 1 | 1 |
| 130958A | Dynascone 10 | 4 | 4 |
| 140220A | Ethyl Aceto Acetate | 4 | 4 |
| 140480A | Ethyl Cinnamate | 1 | 1 |

TABLE 23-continued

FRAGRANCE COMPATIBILITY WITH MINERAL OIL

| Material Code* | Material Name* | 5% | 10% |
|---|---|---|---|
| 140840A | Ethyl Iso Valerate | 1 | 1 |
| 140660A | Ethyl Maltol 10% BB | 2 | 3 |
| 100760A | Ethyl Methyl Phenyl Glycidate | 4 | 4 |
| 140795A | Ethyl Safranate** | 3 | 3 |
| 140860A | Ethyl Vanillin 10% BB** | 1 | 1–2 |
| 140680A | Ethyl-2-methyl Butyrate | 1 | 1 |
| 140880A | Ethylene Brassilate | 1 | 1 |
| 140920A | Eucalyptol | 1 | 1 |
| 140980A | Eugenol | 3 | 3 |
| 141146A | Exolide | 1 | 1 |
| 150002A | Farnesol Synthetic | 1 | 1 |
| 150023A | Fenchyl Acetate | 1 | 2 |
| 150025A | Fenchyl Alcohol | 1 | 1 |
| 150168A | Firbalsam Oliffac abs. 10%/20% IPM | 3 | 3–4 |
| 150200A | Fir Needle Oil Siberian | 1 | 1 |
| 150322A | Florosal Florol | 1 | 1 |
| 150560A | Fructone | 1 | 1 |
| 150570A | Fruitate | 1 | 1 |
| 160310A | Geraniol 8020 | 1 | 1 |
| 160515A | Geranyl Acetate | 1 | 1 |
| 161170A | Gyrane | 1 | 2 |
| 170060A | Hedione | 1 | 1 |
| 170080A | Helional | 3 | 3 |
| 170100A | Heliotropine 10%/20% IPM | 1 | 1 |
| 170228A | Herboxane | 1 | 1 |
| 170240A | Hercolyn | 1 | 1 |
| 170380A | Hexenol, CIS-3 | 1 | 1 |
| 170420A | Hexenyl Acetate, CIS-3 | 1 | 1 |
| 170442A | Hexenyl Iso Butyrate, CIS-3 | 1 | 1 |
| 170520A | Hexenyl Salicylate, CIS-3 | 1 | 1 |
| 170600A | Hexenyl Acetate Alpha | 1 | 1 |
| 170620A | Hexenyl Cinnamic Aldehyde | 1 | 1 |
| 170660A | Hexyl Salicylate** | 1 | 1 |
| 170680A | Hexylene Glycol | 4 | 4 |
| 170940A | Hydroxycitronellal Pure 55 | 3 | 3 |
| 171100A | Hydroxy phenyl butanone 10% BB | 3 | 4 |
| 180040A | Indol 10%/20% IPM** | 1 | 1 |
| 180120A | Ionone Alpha Refined (800 UC) | 1 | 1 |
| 101380A | Isoamyl-N-Butyrate | 1 | 1 |
| 111140A | Isoborneol 10%/20% IPM | 1 | 1 |
| 111180A | Isobornyl Acetate | 1 | 1 |
| 111215A | Isobornyl cyclohexanol 10%/20% IPM | 1 | 1 |
| 123720A | Isocyclocitral | 1 | 1 |
| 250072A | Isopar M | 1 | 1 |
| 251840A | Isopropyl Myristate | 1 | 1 |
| 190323A | Jasmopyrane | 1 | 1 |
| 210352A | Lavandin Oil Grosso Pure | 4 | 4 |
| 211240A | Lilestralis | 1 | 1 |
| 211580A | Linalool Oxide | 1 | 1 |
| 211520A | Linalool Synthetic | 1 | 1 |
| 211620A | Linalyl Acetate Synthetic | 1 | 1 |
| 211920A | Lyral | 2 | 2 |
| 220050A | Magnol** | 1 | 1 |
| 220055A | Majantol | 1 | 1 |
| 220089A | Malusate | 1 | 1 |
| 220190A | Manzanate | 1 | 1 |
| 220305A | Melusat | 1 | 1 |
| 220504A | Methoxy Melonal | 1 | 1 |
| 220520A | Methoxycitronellal | 1 | 1 |
| 220600A | Methyl Anthranilate | 1 | 1 |
| 220660A | Methyl Benzoate | 1 | 1 |
| 220720A | Methyl Chavicol | 1 | 1 |
| 220740A | Methyl cinnamate 10%/20% IPM | 1 | 1 |
| 221076A | Methyl Ionone Gamma Supreme (600 UC) | 1 | 1 |
| 220860A | Methyl Iso Eugenol | 1 | 1 |
| 221300A | Methyl Salicylate | 1 | 1 |
| 100780A | Nonalactone Gamma | 1 | 1 |
| 111081A | Octahydro Coumarin | 1 | 2 |
| 240812A | Orange Terpenes Distilled | 1 | 1 |
| 241120A | Osyrol | 1 | 1 |
| 250707A | Peranat | 1 | 1 |
| 250892A | Phenoxanol | 1 | 1 |
| 250900A | Phenoxy Ethanol | 3 | 4 |
| 250920A | Phenoxy Ethyl Iso Butyrate | 1 | 1 |
| 250940A | Phenyl Acetaldehyde | 4 | 4 |
| 251020A | Phenyl Ethyl Acetate | 1 | 1 |
| 251068A | Phenyl Ethyl Alcohol | 3 | 4 |
| 251320A | Phenyl Propyl Alcohol | 3 | 4 |
| 251739A | Precyclmone B | 1 | 1 |
| 251740A | Prenyl Acetate | 1 | 1 |
| 270460A | Rosalva | 1 | 1 |
| 280720A | Stemone | 1 | 1 |
| 251280A | Styralyl Acetate | 1 | 1 |
| 290320A | Terpineol Alpha | 1 | 1 |
| 290320A | Terpinyl Acetate | 1 | 1 |
| 290448A | Tetrahydro Allo Ocimenol | 1 | 1 |
| 290500A | Tetrahydro Myrcenol | 1 | 1 |
| 290840A | Tetralide 10%/20% IPM** | 1 | 1 |
| 230602A | Trimethyl Hexyl Acetate, 3-5-5 | 1 | 1 |
| 291060A | Triplal | 1 | 1 |
| 291149A | Ultravanil | 4 | 4 |
| 300007A | Undecalactone Gamma | 1 | 1 |
| 300011A | Undecvertol | 1 | 1 |
| 310340A | Vanillin 10% BB | 3 | 4 |
| 37016OU | Veilex #1 | 1 | 1 |
| 37014OU | Veilex #2 | 1 | 1 |
| 37013OU | Veilex #3 | 1 | 1 |
| 310480A | Verdox | 1 | 1 |
| 310500A | Verdyl Acetate | 1 | 1 |
| 310505A | Verdyl Propionate | 1 | 1 |
| 310620A | Vertenex | 1 | 1 |
| 310655A | Vertocinth | 1 | 1 |
| 310660A | Vertofix Coeur | 1 | 1 |

* Fragrance materials were obtained from Bush Boake Allen (BBA), Montvale, NJ, and are designated with the MATERIAL CODE and name used by BBA.

Of the 11 fragrance raw materials that are identified by a double asterisk in Table 23, four are incompatible with mineral oil and the other seven are compatible at 5% and 10% concentration. This indicates that some of the raw materials that are compatible with the mineral oil are incompatible with the ETPA. There are also raw materials that are incompatible with mineral oil but are still compatible in the ETPA gel formulation, indicating that these raw materials are solubilized by the ETPA. This esult indicates that in order for a fragrance component to be incompatible with an ETPA gel formulation, the material must be incompatible with both the mineral oil and the ETPA at the relative concentrations of these materials in the gel formulation.

Example 36

An air freshener was prepared by combining 45 wt. % of ETPA prepared as in Example 3, 35 wt. % Isopar® M (Exxon Chemicals, Houston, Tex.) and 20 wt. % fragrance 564-2432 (BBA, Montvale N.J.). The air freshener was colored by the addition of 0.1% of a 0.2% solution of Pylaklor® Blue (Pylam Products, Tempe Ariz.) dissolved in mineral oil. The result was a crystal clear, hard gel, which was firm enough to stand and hold its shape without a rigid container.

Example 37

A. Inventive Air Freshener Containing ETPA

Figure 2:
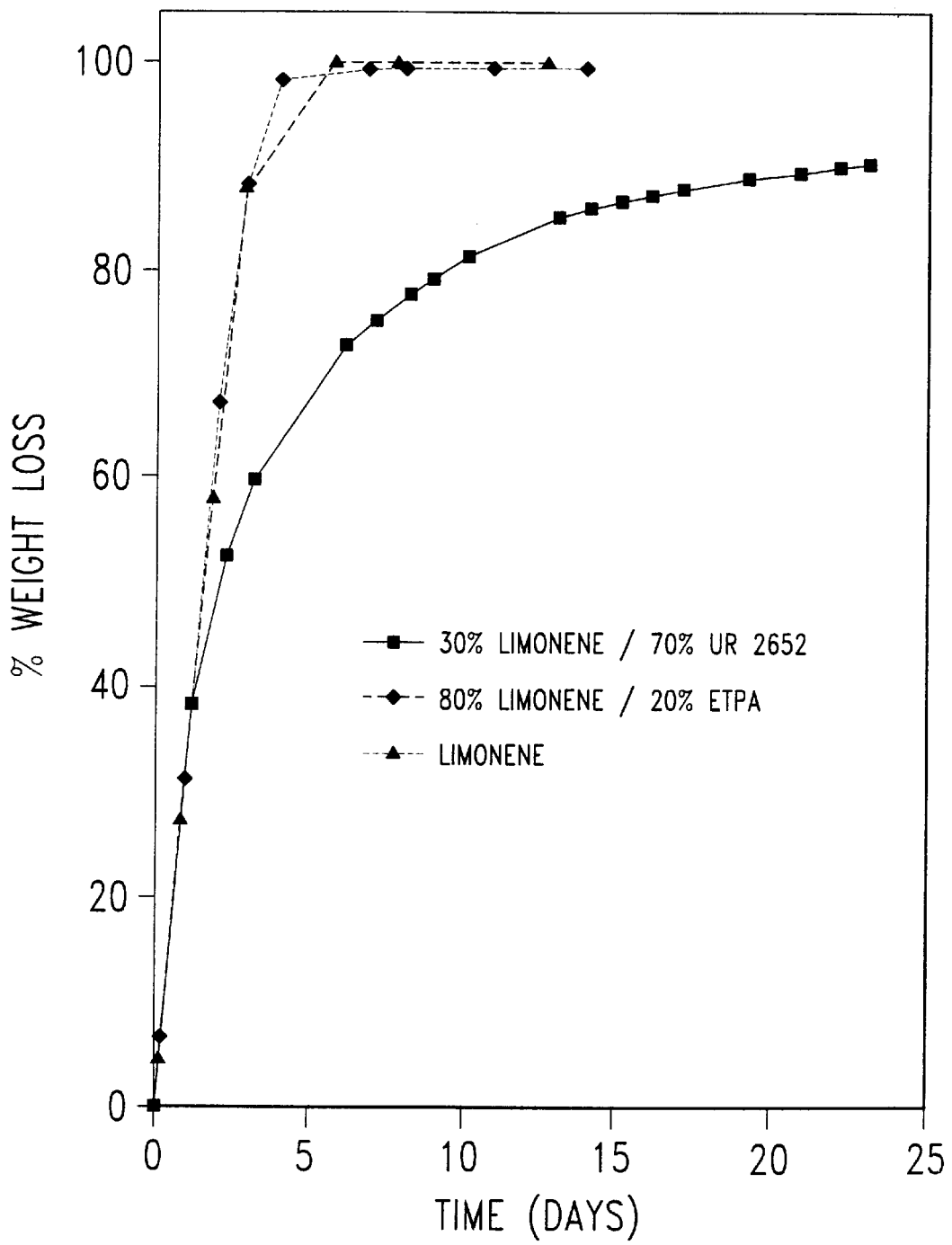
FIG. 2 shows the percent weight loss (based on the initial weight of limonene) as a function of time for a gel of the invention and a comparative gel.

A gel was prepared by heating 20 wt. % of ETPA prepared as in Example 3 and 80 wt. % limonene to form a homogeneous mixture. While cooling, 6 g of the (still molten) gel was poured into an aluminum pan which was covered until the gel had cooled to room temperature. After reaching room temperature, the pan+gel was weighed, and then reweighed periodically to determine the time dependence of weight loss due to evaporation of the limonene. The percent weight loss as a function of time is shown in FIG. 2, where the percent weight loss was calculated based on the initial amount of fragrance in the 6 grams of gel.

B. Comparative Air Freshener Containing Polyamide

A gel was prepared by heating 70 wt. % Uni-Rez® 2652 adhesive grade polyamide resin (Union Camp, Wayne, N.J.) and 30 wt. % limonene to form a homogeneous mixture. This gel has a lower concentration of limonene than the gel prepared in Section A with ETPA because when additional limonene was added to Uni-Rez® 2652 polyamide, the polyamide did not stay in solution. While cooling, 6 g of the (still molten) gel was poured into an aluminum pan which was covered until the gel had cooled to room temperature. After reaching room temperature, the pan+gel was weighed, and then reweighed periodically to determine the time dependence of weight loss due to evaporation of the limonene. The percent weight loss as a function of time is shown in FIG. 2, where the percent weight loss was calculated based on the initial amount of fragrance in the 6 grams of gel.

C. Control

An aluminum pan as used in Sections A and B above was charged with 4.8 g of limonene. The percent weight loss (based on the initial weight of limonene) as a function of time is plotted in FIG. 2.

FIG. 2 shows that limonene is released from a limonene/ETPA gel at about the same rate as limonene evaporates from neat limonene. Also, FIG. 2 shows that essentially all of the limonene originally present in the limonene/ETPA gel is released. In contrast, limonene is released at a relatively slow rate from limonene/Uni-Rez® polyamide, and is only incompletely released even after 20 days.

Example 38

Figure 3:
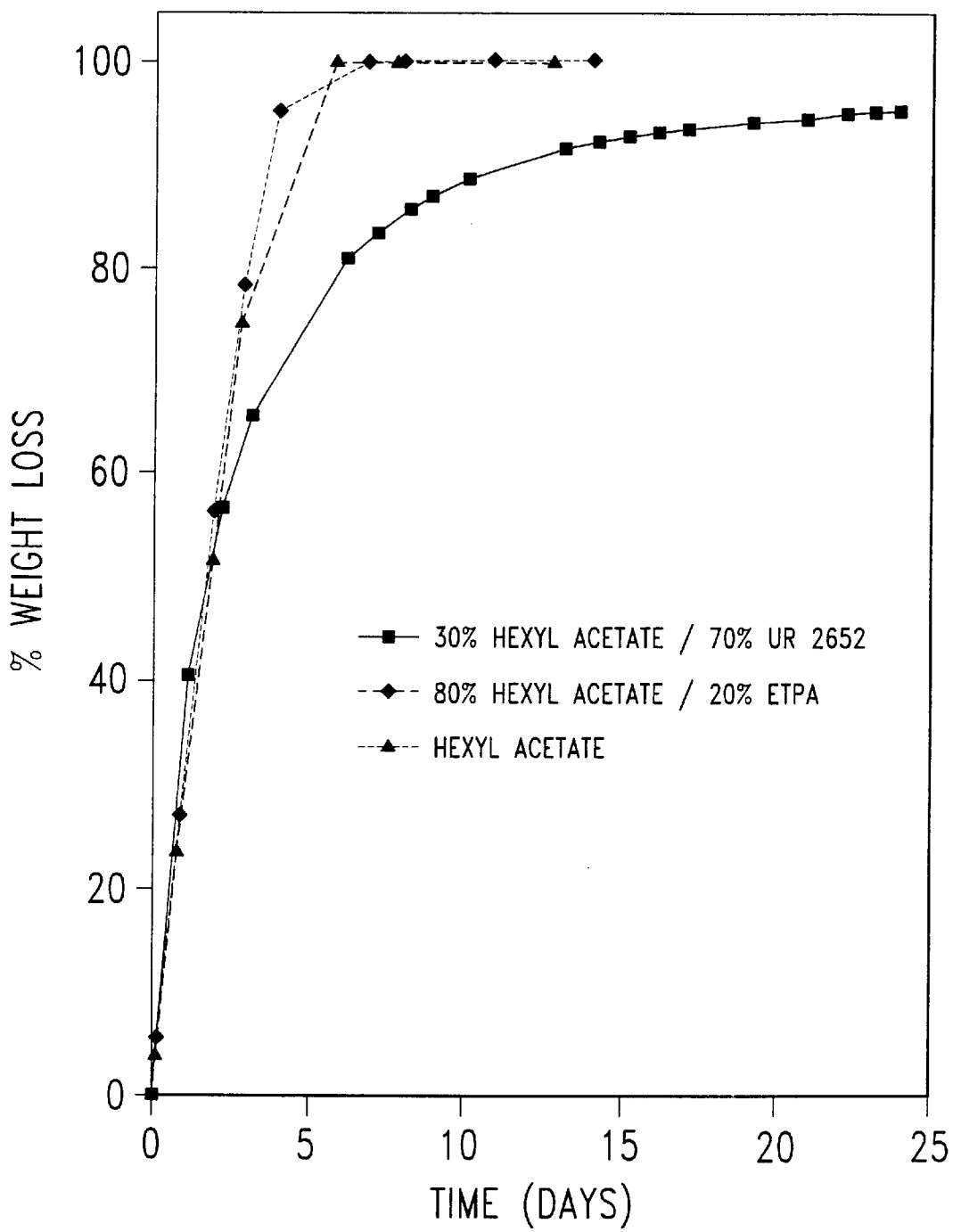
FIG. 3 shows the percent weight loss (based on the initial weight of hexyl acetate) as a function of time for a gel of the invention and a comparative gel.

The experiment described in Example 37 was repeated, with the change that limonene was replaced with a different fragrance material, namely hexyl acetate. The weight loss data is shown in FIG. 3, and essentially repeats the result observed for limonene. Thus, hexyl acetate is slowly and incompletely released from Uni-Rez® 2652 polyamide resin, while being rapidly and completely released from ETPA.

Example 39

Figure 4:
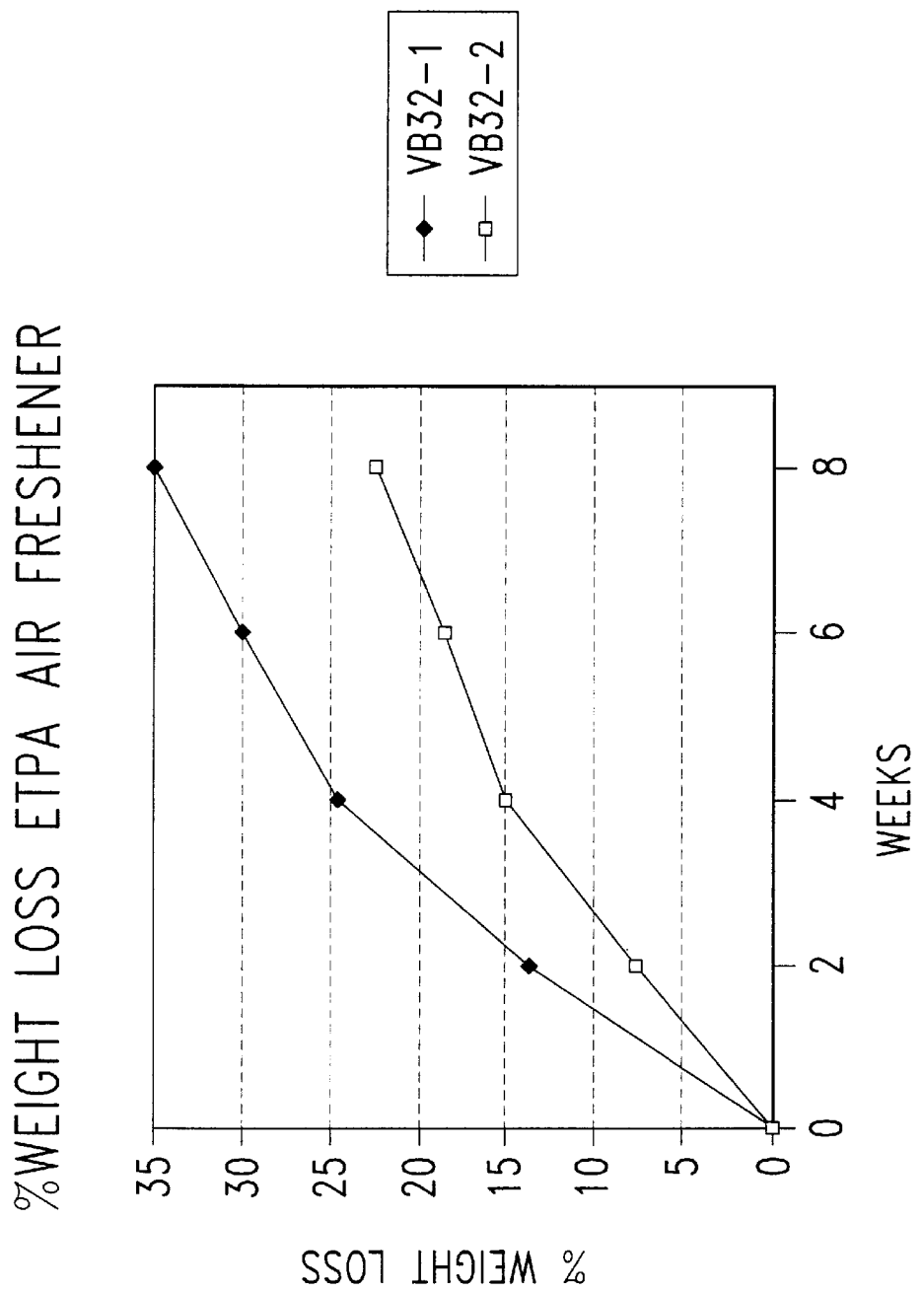
FIG. 4 shows the percent weight loss as a function of time for two gels of the invention, which contain different volatile hydrocarbon components.

A. An air freshener composition was prepared by combining 15 wt. % of the ETPA of Example 8, and 45 wt. % Isopar® M ($C_{13}$–$C_{14}$isoparaffin, Exxon, Houston, Tex.), and heating the mixture to 100° C. Then 20 wt. % Isopar® L ($C_{11}$–$C_{13}$isoparaffin, Exxon, Houston, Tex.), and 20 wt. % fragrance 524-27901 (BBA, Montvale, N.J.) were added, where the wt. % values are based on the entire weight of the composition. The composition was stirred until it became homogeneous and, prior to cooling, 148.26 g of the molten gel was poured into a container weighing 71.12 g, and sealed with a cap weighing 4.59 g. The container was placed into a holder weighing 79.92 g, so that the initial weight of the entire article was 303.69 g. The article was reweighed periodically, and the weight lost divided by the initial weight (times 100) is plotted as a function of time in FIG. 4.

B. An air freshener composition was prepared by combining 15 wt. % of the ETPA polymer of Example 8, and 65 wt. % Isopar® M ($C_{13}$–$C_{14}$isoparaffin, Exxon, Houston, Tex.), and heating the mixture to 100° C. Then 20 wt. % fragrance 524-27901 (BBA, Montvale, N.J.) were added, where the wt. % values are based on the entire weight of the composition. The composition was stirred until it became homogeneous and, prior to cooling, about 150 g of the molten gel was poured into a container to form an article. The article was weighed periodically, and the weight lost divided by the initial weight (times 100) is plotted as a function of time in FIG. 4.

Example 40

An air freshener was prepared by combining 63 wt. % of the ETPA resin prepared in Example 8 and 25.6 wt. % Isopar® M ($C_{13}$–$C_{14}$isoparaffin, Exxon, Houston, Tex.) and heating this mixture to 100° C. with stirring until uniform. The temperature was reduced to 90° C., and then 10 wt. % fragrance 321-28856 (BBA, Montvale, N.J.), 1 wt. % D&C yellow #10 and 0.4 wt. % D&C green #5 dye were added (Pylam Products, Tempe Ariz.). After mixing until uniform, the mixture was poured into a star-shaped mold. After the gel had almost completely set up, it was coated with a mixture of 20 wt. % Uni-Rez 2620 polyamnide resin (Union Camp, Wayne N.J.) dissolved in n-propanol.

Example 41

An air freshener was prepared by combining 63 wt. % of the ETPA resin prepared in Example 8 and 26.8 wt. % Isopar® M ($C_{13}$–$C_{14}$isoparaffin, Exxon, Houston, Tex.) and heating this mixture to 100° C. with stirring until uniform. The temperature was reduced to 90° C., and then 10 wt. % fragrance 522-28855 (BBA, Montvale, N.J.), and 0.2 wt. % Pylakrome Red (Pylam Products, Tempe Ariz.) were added. After mixing until uniform, the mixture was poured into a heart-shaped mold. After the gel had almost completely set up, it was coated with a mixture of 20 wt. % Uni-Rez 2620 polyamide resin (Union Camp, Wayne N.J.) dissolved in n-propanol.

Example 42

A fragrance stick was prepared by combining 40 wt. % of ETPA as prepared in Example 3 with 45 wt. % Drakeol® 7 mineral oil (Penreco, a division of Pennzoil Products Company, Kearns City, Pa.), heating the mixture until homogeneous (about 100° C.) and then adding 15 wt. % fragrance 141-27669 (BBA, Montvale, N.J.). Upon cooling, the composition had a crystal-clear appearance with a stick-like consistency which was fairly hard. Upon application to the skin, the residue had a somewhat greasy feel. Also, the amount of material that was applied to the skin using a reasonable amount of force was somewhat less than desired, ie., the pay-off was too slow.

Example 43

A fragrance stick was prepared by combining 30 wt. % of ETPA as prepared in Example 3 with 55 wt. % Drakeol® 7 mineral oil, heating the mixture until homogeneous (about 100° C.) and then adding 15 wt. % fragrance 141-27669 (BBA, Montvale, N.J.). Upon cooling, the composition had a crystal-clear appearance with a stick-like consistency which was not as hard as the stick of Example 42. Upon application to the skin, the residue had a somewhat greasy feel, however the pay-off was excellent.

Example 44

A fragrance gel was prepared by combining 20 wt. % of ETPA as prepared in Example 3 with 65 wt. % Drakeol® 7 mineral oil, heating the mixture until homogeneous (about 100° C.) and then adding 15 wt. % fragrance 141-27669 (BBA, Montvale, N.J.). The fragrance gel had the consistency of gelatin, however when a finger was dipped into the gel, the gel slightly melted and left a residue on the finger. This product would be suitably placed into a container. Upon application to the skin, the residue had a greasy feel.

Example 45

A fragrance gel was prepared by combining 20 wt. % of ETPA as prepared in Example 3 with 65 wt. % Isopar® M paraffins, heating the mixture until homogeneous (about 100° C.) and then adding 15 wt. % fragrance 141-27669 (BBA, Montvale, N.J.). The fragrance gel had the consistency of gelatin, however when a finger was dipped into the gel, the gel slightly melted and left a residue on the finger. This product would be suitably placed into a container. Upon application to the skin, the residue did not have a greasy feel.

Example 46

A fragrance stick was prepared by combining 30 wt. % of ETPA as prepared in Example 3 with 55 wt. % Isopar® M paraffins, heating the mixture until homogeneous (about 100° C.) and then adding 15 wt. % fragrance 141-27669 (BBA, Montvale, N.J.). Upon cooling, the composition had a crystal-clear appearance with a hard, stick-like consistency which was not as hard as the stick of Example 42. Upon application to the skin, the residue dried quickly and did not feel greasy. Also, the pay-off was excellent and the composition was crystal clear.

Example 47

A fragranced soft gel was prepared by combining 20 wt. % of ETPA as prepared in Example 3 with 55 wt. % Isopar® M paraffins, heating the mixture until homogeneous (about 100° C.) and then adding 25 wt. % 040-27273 fragrance (BBA, Montvale N.J.). The gel solidified at about 35° C. to form a soft composition that displayed syneresis.

Example 48

A fragranced soft gel was prepared by combining 30 wt. % of ETPA as prepared in Example 3 with 45 wt. % Isopar® M paraffins, heating the mixture until homogeneous (about 100° C.) and then adding 25 wt. % 040-27016 fragrance (BBA, Montvale N.J.). The gel solidified at 45° C. to form a stick having a desirably firm consistency, which did not display syneresis, and was almost crystal clear.

Example 49

A fragranced soft gel was prepared by combining 30 wt. % of ETPA as prepared in Example 3 with 45 wt. % Isopar® M paraffins, heating the mixture until homogeneous (about 100° C.) and then adding 25 wt. % 040-27016 fragrance (BBA, Montvale N.J.). The gel solidified at 45° C. to form a stick which had a desirably firm consistency, did not display syneresis, was almost clear and had good pay-off.

Example 50

A fragranced soft gel was prepared by combining 30 wt. % of ETPA as prepared in Example 3 with 45 wt. % Isopar® M paraffins, heating the mixture until homogeneous (about 100° C.) and then adding 25 wt. % 640-22203 fragrance (BBA, Montvale N.J.). The gel solidified at 45° C. to form a stick with a desirably firm consistency which was also cloudy. This soft gel used a different fragrance than the soft gel of Example 49, demonstrating the selection of the fragrance is important in determining whether a clear or cloudy gel will be produced.

Example 51

A fragranced soft gel was prepared by combining 30 wt. % of ETPA as prepared in Example 3 with 55 wt. % Isopar® M paraffins, heating the mixture until homogeneous (about 100° C.) and then adding 15 wt. % 141-27669 fragrance (BBA, Montvale N.J.). The gel solidified at 50–55° C. to form a stick which had a desirably firm consistency and excellent rub-off properties onto skin. The stick was clear.

Example 52

An insect stick was prepared by combining 45 wt. % of ETPA as prepared in Example 3 with 39.5 wt. % Isopar® M (Exxon Chemicals, Houston, Tex.), 15 wt. % DEET (Morflex, Greensboro, N.C.), 0.5 wt. % fragrance 564-24392 (BBA, Montvale, N.J.) and 0.5% of a 0.2 wt. % solution of Pylakrome Blue (Pylam Products, Tempe Ariz.) in mineral oil. These ingredients were taken to elevated temperature (about 100° C.) and stirred until a homogeneous mixture resulted. Upon cooling, the composition had a clear appearance with a stick consistency, which could be rubbed onto the skin or other surface to provide a thin film with insect-repelling properties.

Example 53

An insect stick was prepared by combining 45 wt. % of ETPA as prepared in Example 3 with 53 wt. % Isopar® M (Exxon Chemicals, Houston, Tex.), 1 wt. % Prallethrin 90% (McLaughlin Gormley King Company, Minneapolis, Minn.) and 1 wt. % fragrance 564-24392 (BBA, Montvale, N.J.). These ingredients were taken to elevated temperature (about 100° C.) and stirred until a homogeneous mixture resulted. Upon cooling, the composition had a clear appearance with a stick consistency, which could be rubbed onto a surface (such as the floor or cupboard) to provide a thin film with insect-killing properties.

Example 54

Gelled Body With Coating

A gel was formed from 45 wt. % of the ETPA of Example 3, 50 wt. % mineral oil (Drakeol® 7 from Penreco) and 5 wt. % fragrance (product number 564-24392 from Bush Boake Allen of Montvale, N.J.). A wick was inserted while the gel cooled, to provide a crystal clear candle with excellent consistency.

The candle was coated as set forth in Table 24, with the coating compositions set forth in Column 1. The Uni-Rez® 2620 and 2970 polyamide resins, the Uni-Rez® R-100 rosin ester and the Micromid® 321 aqueous polyamide dispersion were obtained from Union Camp Corporation, Wayne, N.J. Epolene® C-16 is a polyethylene wax from Eastman Chemicals. E-1498 is a hydrocarbon resin from Exxon Chemicals. In Table 24, "X35-659-22" is a polyamide prepared from 70.14 parts Empol® 1008 hydrogenated dimer, 19.76 parts stearic acid, 0.12 parts azelaic acid, 9.02 parts ethylene diamine and 0.95 parts hexamethylene diamine, in a manner analogous to that described in Example 1.

A candle was dipped into each of the coating composition described in column 1 of Table 24, at either 140° C. for neat molten resin or at room temperature for the solution coating compositions. Each coating was characterized qualitatively in terms of clarity, hardness and whether the coating adhered well to the candle.

TABLE 24

COATINGS USED ON GELLED BODIES AND PROPERTIES THEREOF

| Coating System | Clarity | Hardness | Comments |
|---|---|---|---|
| X35-659-22 (neat) | clear | good | coats well |
| Uni-Rez ® 2970 (neat) | clear | brittle | coats well |
| Epolene ® C-16 (neat) | hazy | soft | no adhesion |
| E-1498 (neat) | clear | brittle | coats well |
| Uni-Rez ® R-100 (neat) | clear | brittle | coats well |
| 20 wt. % Uni-Rez 2620 in n-propanol (solution) | clear | good | coats well |
| 10 wt. % X35-659-22 in n-propanol (solution) | clear | good | coats well |
| Micromid ® 321 | hazy | good | coats poorly |
| Micromid ® 321 + 10 wt. % n-propanol | hazy | good | coats well |

Example 55

Clarity Measurement

The clarity test consisted of shining white light through a sample of a given thickness at room temperature and determining the diff-use transmittance and the total transmittance for the sample. The percent haze for a sample was calculated by % haze=(diffuse transmittance/total transmittance)×100

Samples were made by melting the substance to be evaluated and pouring the melt into 50 mm diameter molds. The samples were made at two thicknesses, 5.5±0.4 mm and 2.3±0.2 mm. The compositions identified in Table 25 were evaluated in this manner.

TABLE 25

GELS AND WAXES USED FOR CLARITY MEASUREMENTS

| Sample | Manufacturer |
|---|---|
| paraffin wax (CAS 8002-74-2) | Aldrich Chemical (Milwaukee, WI) |
| beeswax chips | Mangelsen's (Omaha, NE) |
| wax crystals (Frosty White #51212) | Distlefink Designs Newton, NJ) |
| 50% ETPA X35-879-48[1] in Drakeol 7 (Penreco) | Union Camp (Wayne, NJ) |
| 20% Kraton ® G1650 (Shell) in Drakeol 7[2] | Penzoil (Houston, TX) |

1. ETPA from Example 26
2. Example 2 from WO 97/08282

The clarity measurements were made on a Hunter Lab Ultrascan Sphere Spectrocolorimeter using the following settings: Specular Included; UV off; Large area of view; Illuminate D65; Observer 10°; and Standardized for total transmittance.

The percent haze values for samples prepared as described above are given in Table 26. The standard wax (paraffin) used in traditional candles had haze values greater than 93% regardless of sample thickness. The Kraton® samples had very low haze values (<15%), where the thicker sample had a larger haze value. The thicker Kraton® sample appeared to have a large number of air bubbles trapped in the sample, which may have increased the haze slightly. The ETPA samples had higher haze values than the Kraton® samples (<43%), and appeared to be thickness dependent. However, the surfaces of the ETPA samples appeared to be smudged. When the smudges were removed from the thicker sample, the haze value decreased from about 43% to about 5%. Therefore, the clarity of the ETPA samples is very dependent on the sample having unsmudged surfaces.

TABLE 26

CLARITY MEASUREMENTS ON GELS AND WAXES

| Sample | Thickness (mm) | % Haze |
|---|---|---|
| paraffin wax | 2.1 | 94.2 |
| paraffin wax | 5.0 | 93.3 |
| beeswax | 2.2 | 93.6 |
| beeswax | 5.2 | 93.2 |
| wax crystals | 2.5 | 94.3 |
| wax crystals | 5.3 | 94.2 |
| Kraton ® | 2.1 | 14.5 |
| Kraton ® | 5.8 | 9.0 |
| ETPA | 2.3 | 27.2 |
| ETPA | 6.0 | 42.9 |
| ETPA (smudges removed) | 6.0 | 4.7 |

Example 56

Rigidity Measurement

The rigidity test consisted of determining the amount of deflection due to gravity of a given sized sample at room temperature. Samples of Kraton® and ETPA resins as defined in Table 25 were cast into 57×10×3 mm samples. These samples were then secured on a horizontal surface using a weight, and the deflection angle was measured as shown in FIG. 5. The deflection angle (θ) is calculated by measuring x and y, and using the expression $$\theta = \arctan(x/y)$$

where θ=0° is defined as no deflection and θ=90° is defined as the maximum deflection.

The observed deflection angle for the Kraton® and ETPA resin samples is given in Table 27. The Kraton® sample deflected about 80° while there was no visible deflection of the ETPA gel sample.

TABLE 27

DEFLECTION ANGLES OF TWO GELS

| Sample | θ (°) |
|---|---|
| Kraton ® | 79 ± 3 |
| ETPA | ~0 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A flammable article comprising a fuel and a solid coating, where the coating encases at least a portion of the fuel.

2. The article of claim 1 further comprising a wick, the wick at least partially encased within the fuel.

3. The article of claim 1 wherein the fuel comprises a wax.

4. The article of claim 1 wherein the fuel comprises about 80 to 99 wt. % of a hydrocarbon oil, and about 1 to 20 wt. % of a blend of at least two different polymer members selected from the group consisting of diblock copolymers, triblock copolymers, radial block copolymers and multiblock copolymers, said composition including at least one diblock copolymer and at least one triblock copolymer, with said diblock and triblock polymers comprising segments of styrene monomer units and rubber monomer units.

5. The article of claim 1 wherein the fuel comprises from about 70% to about 98% by weight of a hydrocarbon oil, from about 2% to about 30% by weight a copolymer selected from the group consisting of a triblock, radial block and multiblock copolymer, and from 0 to about 10% by weight of a diblock copolymer.

6. The article of claim 1 wherein the fuel comprises a gel.

7. The article of claim 6 wherein the gel comprises a gellant and a flammable solvent.

8. The article of claim 7 wherein the gel has a deflection value of less than 70.

9. The article of claim 7 wherein the solvent has a flash point ranging from about −15° C. to about 300° C.

10. The article of claim 7 which is a candle.

11. The article of claim 7 wherein the solvent comprises hydrocarbon oil.

12. The article of claim 7 wherein the gellant is selected from a group consisting of polyamide resin, ester-terminated dimer acid-based polyamide (ETDABP) resin and a block copolymer.

13. The article of claim 12 wherein the polyamide resin is the reaction product of reactants comprising dimer acid and diamine, the ester-terminated dimer acid-based polyamide resin is the reaction product of reactants comprising dimer acid, diamine and monoalcohol, and the block copolymer is a styrene-butadiene-styrene or styrene-isoprene-styrene block copolymer.

14. The article of claim 1 wherein the coating comprises a polymer selected from the group of thermoplastic polymer and thermoset polymer.

15. The article of claim 14 wherein the thermoplastic polymer is selected from polyamide resin, ester-terminated dimer acid-based polyamide resin and styrene-acrylic resin.

16. The article of claim 1 wherein the coating is transparent.

17. The article of claim 16 wherein the article is transparent.

18. The article of claim 1 further comprising an optional component selected from fragrance, insect repellent, insecticide, UV-inhibitor and antioxidant.

19. The article of claim 18 wherein UV-inhibitor is present within the coating.

20. The article of claim 1 further comprising a wick and in the form of a candle, wherein the fuel is a gel comprising mineral oil and a gellant, the gellant comprising ester-terminated dimer acid-based polyamide, the fuel and the coating being transparent.

21. A flammable article comprising a gel, the gel comprising a gellant and a flammable solvent, the gellant comprising ester-terminated dimer acid-based polyamide (ETDABP).

22. The article of claim 21 wherein the gel is transparent.

23. The article of claim 21 wherein the gel has a deflection angle of less than 70.

24. The article of claim 21 wherein the gel does not exhibit syneresis.

25. The article of claim 21 which is free-standing.

26. The article of claim 21 which is positioned within a container.

27. The article of claim 21 further comprising a wick, the wick at least partially encased by the gel, the article being in a form of a candle.

28. The candle of claim 27 wherein the solvent comprises mineral oil.

29. The article of claim 21 wherein the ETDABP contributes 10–95%, and the solvent contributes 5–90% of the combined weight of the ETDABP and the solvent.

30. The article of claim 21 further comprising at least one optional component selected from fragrance, colorant, insect repellent, insecticide, antioxidant and UV-inhibitor.

31. The article of claim 30 wherein the ETDABP contributes 30–60%, the solvent contributes 40–70%, the fragrance contributes less than 50% and the colorant contributes less than 5% of the combined weight of the ETDABP, solvent, fragrance and colorant.

32. The article of claim 30 wherein the ETDABP contributes 10–30%, the solvent contributes 65–80%, the fragrance contributes less than 50% and the colorant contributes less than 1% of the combined weight of the ETDABP, solvent, fragrance and colorant.

33. The article of claims 21 wherein the ETDABP has an amide:ester ratio of from 9:1 to 1:1.

34. The article of claims 12 or 21 wherein the ETDABP has the formula (1):

$$R^1-O\left[\overset{O}{\underset{}{C}}-R^2-\overset{O}{\underset{}{C}}N-R^3-N\atop \underset{R^{3a}}{} \quad \underset{R^{3a}}{}\right]_n \overset{O}{\underset{}{C}}-R^2-\overset{O}{\underset{}{C}}-O-R^1 \quad (1)$$

wherein, n designates a number of repeating units such that ester groups constitute from 10% to 50% of the total of the ester and amide groups;

$R^1$ at each occurrence is independently selected from hydrocarbyl groups;

$R^2$ at each occurrence is independently selected from a $C_{2-42}$ hydrocarbon group with the proviso that at least 10% of the $R^2$ groups have 30–42 carbon atoms;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$.

35. The article of claim 34 wherein, $R^1$ at each occurrence is independently selected from an alkyl or alkenyl group containing at least 4 carbon atoms;

$R^2$ at each occurrence is independently selected from a $C_{4-42}$ hydrocarbon group with the proviso that at least 50% of the $R^2$ groups have 30–42 carbon atoms; and $R^{3a}$ at each occurrence is independently selected from hydrogen, $C_{1-10}$alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen.

36. The candle of claim 34 wherein ester groups constitute from 20% to 35% of the total of the ester and amide groups.

37. The article of claim 34 wherein $R^1$ is a $C_{12-22}$alkyl group and $R^2$ is a $C_{30-42}$ hydrocarbon group having the structure of polymerized fatty acid with the carboxylic acid groups removed.

38. The article of claim 34 wherein between 1% and 50% of the $R^2$ groups are a $C_{4-19}$ hydrocarbon group, $R^3$ is a $C_{2-36}$ hydrocarbon group and $R^{3a}$ is hydrogen.

39. The article of claim 34 wherein $R^{3a}$ is hydrogen and at least 1% of the $R^3$ groups are polyalkylene oxide.

40. The article of claim 34 wherein at least 1% of the $—N(R^{3a})—R^3—N(R^{3a})—$ groups are independently selected from polyakylene amine,

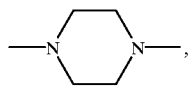

and

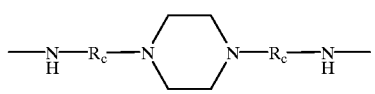

wherein $R_c$ is a $C_{1-3}$alkyl group.

41. The article of claim 21 further comprising a solid coating overlying at least of portion of the article.

42. The article of claim 41 wherein the coating comprises dimer-acid-based polyamide resin.

43. An article comprising flammable solvent with a flash point ranging from about −15° C. to about 300° C. and an ester-terminated polyamide of formula (1)

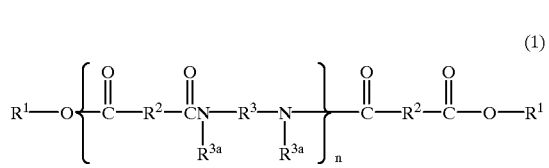

wherein n designates a number of repeating units such that ester groups constitute from 10% to 50% of the total of the ester and amide groups;

$R^1$ at each occurrence is independently selected from an alkyl or alkenyl group containing at least 4 carbon atoms;

$R^2$ at each occurrence is independently selected from a $C_{4-42}$ hydrocarbon group with the proviso that at least 50% of the groups have 30–42 carbon atoms;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}—N—R^3$, such that at least 50% of the $R^{3a}$ groups are hydrogen.

44. The article of claim 43 further comprising a wick.

45. The article of claim 43 wherein the flash point ranges from about 40° C. to about 90° C.

46. The article of claim 43 further comprising a coating overlying at least a portion of the article's surface.

47. The article of claim 46 wherein the coating comprises dimer acid-based polyamide.

48. A flammable article comprising ester-terminated dimer acid-based polyamide (ETDABP) and solvent, the solvent having a flash point ranging from about −15° C. to about 300° C. and the ester-terminated dimer acid-derived polyamide being prepared by a method comprising reacting x equivalents of carboxylic acid from diacid or a reactive equivalent thereof, y equivalents of amine from diamine and z equivalents of hydroxyl from monoalcohol or a reactive equivalent thereof, wherein at least about 10% of the carboxylic acid equivalents are from polymerized fatty acid, and monoalcohol is substantially the only monofinctional reactant used to form the gellant, wherein each of x, y and z is greater than 0.

49. The article of claim 48 further comprising a wick.

50. The article of claim 48 wherein $0.9 \leq \{x/(y+z)\} \leq 1.1$, and $0.1 \leq \{z/(y+z)\} \leq 0.7$.

51. The article of claim 48 further comprising a coating overlying at least a portion of the surface thereof.

52. The article of claim 51 wherein the coating comprises dimer acid-based polyamide.

53. The article of claim 48 further comprising an optional component selected from the group consisting of fragrance, insect repellent, insecticide, antioxidant and UV-inhibitor.

54. A composition that emits an active substance over an extended period comprising ester-terminated dimer acid-based polyamide (ETDABP) and an active substance, the composition having a consistency of a gel.

55. The composition of claim 54 wherein the ETDABP has the formula

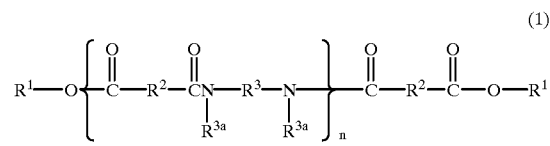

wherein n designates a number of repeating units such that ester groups constitute from 10% to 50% of the total of the ester and amide groups;

$R^1$ at each occurrence is independently selected from hydrocarbyl groups;

$R^2$ at each occurrence is independently selected from a $C_{2-42}$ hydrocarbon group with the proviso that at least 10% of the $R^2$ groups have 30–42 carbon atoms;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}—N—R^3$.

56. The composition of claim 54 wherein the active substance is a fragrance.

57. The composition of claim 56 wherein the fragrance is selected from menthol, methyl salicylate and eucalyptus.

58. The composition of claim 54 present within a container.

59. The composition of claim 54 wherein the active substance is selected from an insecticide and an insect-repellent.

60. The composition of claim 54 wherein the gel has a surface, and a solid polymer coating overlies at least a portion of the surface.

61. The composition of claim 54 which is self-supporting.

62. The composition of claim 54 in the form of a stick.

63. The composition of claim 54 which is transparent.

64. The composition of claim 54 further comprising a colorant.

65. The composition of claim 54 comprising ETDABP in a concentration range of about 5–60 wt. %, and fragrance in a concentration range of about 1–50 wt. %, where these weight percent values are based on the total weight of the composition.

66. The composition of claim 54 comprising mineral oil.

67. The composition of claim 54 comprising fatty ester.

68. A method of forming a coated article comprising the steps (a) providing a gel structure having an exterior surface; and (b) applying a coating to the exterior surface.

69. The method of claim 68 wherein the coating is applied by any of (a) spraying the coating onto the exterior surface;

(b) dipping the gel structure into a solvent-containing coating composition; or (c) dipping the gel structure into a solvent-free molten coating composition.

* * * * *

UNITED STATES PATENT AND TRADEMARK OFFICE
CERTIFICATE OF CORRECTION

PATENT NO : 6,111,055
DATED : August 29, 2000
INVENTOR(S) : Vivian Berger et al.

It is certified that errors appear in the above-identified patent and that said Letters Patent are hereby corrected as shown below:

Claim 33, column 60, line 18, "claims 21" should read --claim 21--.
Claim 41, column 61, line 24, "at least of portion of" should read --at least a portion of--.
Claim 43, column 61, line 48, "50% of the groups" should read --50% of the $R_2$ groups--.

Signed and Sealed this

Fifteenth Day of May, 2001

Attest:

NICHOLAS P. GODICI

Attesting Officer     Acting Director of the United States Patent and Trademark Office